United States Patent
Polley et al.

(10) Patent No.: US 10,570,363 B2
(45) Date of Patent: Feb. 25, 2020

(54) SYSTEM AND METHOD FOR REGULATING CELL CULTURE BASED PRODUCTION OF BIOLOGICS

(71) Applicant: Lonza Limited, Visp (CH)

(72) Inventors: Rex Polley, Exeter, NH (US); Matthew Sarcopski, Atlanta, GA (US); Robert Horton, Lee, NH (US); Thomas Ellis, Stratham, NH (US); Paul Pease, Durham, NH (US); John Chapin, Portsmouth, NH (US)

(73) Assignee: Lonza Ltd., Visp (CH)

( * ) Notice: Subject to any disclaimer, the term of this patent is extended or adjusted under 35 U.S.C. 154(b) by 369 days.

(21) Appl. No.: 15/294,152

(22) Filed: Oct. 14, 2016

(65) Prior Publication Data

US 2017/0107476 A1    Apr. 20, 2017

Related U.S. Application Data

(60) Provisional application No. 62/242,758, filed on Oct. 16, 2015.

(51) Int. Cl.
  *C12M 1/36*     (2006.01)
  *C12Q 3/00*     (2006.01)
  *G01N 30/86*    (2006.01)

(52) U.S. Cl.
  CPC ............. *C12M 41/48* (2013.01); *C12Q 3/00* (2013.01); *G01N 30/8651* (2013.01); *G01N 30/8662* (2013.01)

(58) Field of Classification Search
  None
  See application file for complete search history.

(56) References Cited

U.S. PATENT DOCUMENTS 7,379,783 B2    5/2008  Popp
7,379,784 B2    5/2008  Popp
(Continued)

FOREIGN PATENT DOCUMENTS

WO    WO 2010/002745 A1    1/2010
WO    WO 2010/036760 A1    4/2010
(Continued)

OTHER PUBLICATIONS

International Preliminary Report on Patentability (PCT/IB/326 & PCT/IB/373) issued in PCT Application No. PCT/US2016/057128 dated Apr. 26, 2018, including English translation of document C1 previously filed Mar. 17, 2018 (eleven (11) pages).
(Continued)

*Primary Examiner* — Richard C Gurtowski
(74) *Attorney, Agent, or Firm* — Crowell & Moring LLP

(57) ABSTRACT

The disclosure is directed to a system and method for control of at least one bioreactor, other cell cultivation-related equipment, and systems containing any combination of these in a plant. For example, a Plant-Wide Control System (PWCS) or a Process Control System (PCS) may be divided into three main components: hardware (including operating systems, such as a controller communicating with one or more servers of a network associated with the PWCS, (2) software (such as a control module) for performing control, and (3) one or more instrument control loops, which may be used by the software to maintain certain process values. Moreover, a Height Equivalent of a Theoretical Plate (HETP) value and an asymmetry factor may be determined based on real-time analysis on a chromatography column, using PWCS components.

7 Claims, 17 Drawing Sheets

(56) References Cited

U.S. PATENT DOCUMENTS

| | | |
|---|---|---|
| 7,392,107 B2 | 6/2008 | Popp |
| 7,428,442 B2 | 9/2008 | Popp |
| 7,444,197 B2 | 10/2008 | Popp |
| 7,471,991 B2 | 12/2008 | Popp |
| 7,509,185 B2 | 3/2009 | Popp |
| 7,799,273 B2 | 9/2010 | Popp |
| RE43,527 E | 7/2012 | Popp |
| 8,410,928 B2 | 4/2013 | Ganguly et al. |
| 8,491,839 B2 | 7/2013 | Popp |
| 8,591,811 B2 | 11/2013 | Popp |
| 8,660,680 B2 | 2/2014 | Popp |
| 9,008,815 B2 | 4/2015 | Popp |
| 9,092,028 B2 | 7/2015 | Popp |
| 9,195,228 B2 | 11/2015 | Popp |
| 9,304,509 B2 | 4/2016 | Popp |
| 2005/0158701 A1 | 7/2005 | West |
| 2009/0205409 A1 | 8/2009 | Ciavarini et al. |
| 2010/0127860 A1 | 5/2010 | Ganguly et al. |
| 2011/0060463 A1 | 3/2011 | Selker et al. |
| 2011/0136225 A1 | 6/2011 | Vunjak-Novakovic et al. |
| 2013/0218352 A1 | 8/2013 | Iovanni et al. |
| 2014/0067308 A1 | 3/2014 | Cunnien et al. |
| 2015/0260693 A1 | 9/2015 | DeMarco |
| 2016/0041551 A1 | 2/2016 | Popp |

FOREIGN PATENT DOCUMENTS

| | | |
|---|---|---|
| WO | WO 2012/021681 A2 | 2/2012 |
| WO | WO 2013/028828 A1 | 2/2013 |
| WO | WO 2014/043602 A2 | 3/2014 |

OTHER PUBLICATIONS

International Search Report and Written Opinion (PCT/ISA/220, PCT/ISA/210, and PCT/ISA/237) issued in PCT Application No. PCT/US2016/057128 dated Jan. 10, 2017 (12 pages).

Extended European Search Report issued in counterpart European Application No. 16856310.4 dated Apr. 25, 2019 (15 pages).

Extended European Search Report issued in counterpart European Application No. 16856310.4 dated Sep. 26, 2019 (15 pages).

Israeli Office Action issued in counterpart Israeli Application No. 258633 dated Dec. 22, 2019 with partial English translation (five (5) pages).

1300

1400

US 10,570,363 B2

SYSTEM AND METHOD FOR REGULATING CELL CULTURE BASED PRODUCTION OF BIOLOGICS

CROSS REFERENCE TO RELATED APPLICATIONS

This application claims priority to and the benefit of U.S. Provisional Application No. 62/242,758, filed Oct. 16, 2015, the contents of which are incorporated herein by reference.

BACKGROUND ART

The invention relates to a system and method for control of at least one bioreactor, other cell cultivation-related equipment, and systems containing any combination of the same.

Cell culture processes are used for cultivating various types of cells, such as mammalian cells. For example, a cell culture process may be implemented via a bioreactor. It is important in cell culture processes to maintain the proper physicochemical environment for maximum cell cultivation (cells such as Human cells, Chinese Hamster Ovary (CHO) cells, mouse myeloma (NS0), hybridoma), and/or producing the desired product (such as recombinant protein, a monoclonal antibody, antibody fusion protein and other related product types) meeting its quality specifications. For example, factors such as dissolved oxygen levels, culture pH, temperature, shear sensitivity and the like play important roles in the cell culture process. Moreover, the maintenance of the nutritional environment is also important.

However, in the context of producing or cultivating these multiple different cells on a large, industrial scale, maintaining the proper levels of the physicochemical and/or the nutritional environment may be challenging, especially given that a large-scale cultivation system may not only require a plurality of bioreactors, but would also require other types of equipment, e.g., preparation equipment, feed equipment, purification equipment, etc., to carry out the various tasks involved in cell cultivation. In this regard, systems and/or methods for maintaining proper environments for cell cultivation in a large scale bioreactor implementation and allowing for operator/user interaction with the implementation are needed.

SUMMARY OF THE INVENTION

In accordance with one or more aspects of the disclosure, the invention is directed to a system and method for control of at least one bioreactor, other cell cultivation-related equipment, and systems containing any combination of these in a plant. For example, a Plant-Wide Control System (PWCS) or a Process Control System (PCS) may be divided into three main components: (1) hardware (including operating systems, such as a controller communicating with one or more servers of a network associated with the PWCS, (2) software (such as a control module) for performing control, and (3) one or more instrument control loops, which may be used by the software to maintain certain process values. Moreover, a Height Equivalent of a Theoretical Plate (HETP) value and an asymmetry factor may be determined based on real-time analysis on a chromatography column, using PWCS components. Accordingly, the HETP, peak asymmetry and peak efficiency values can be, for example, calculated in real-time using the hardware/software that already exists for controlling the chromatography system without having to dedicate special hardware or software.

DETAILED DESCRIPTION OF EMBODIMENTS OF THE INVENTION

Figure 1:
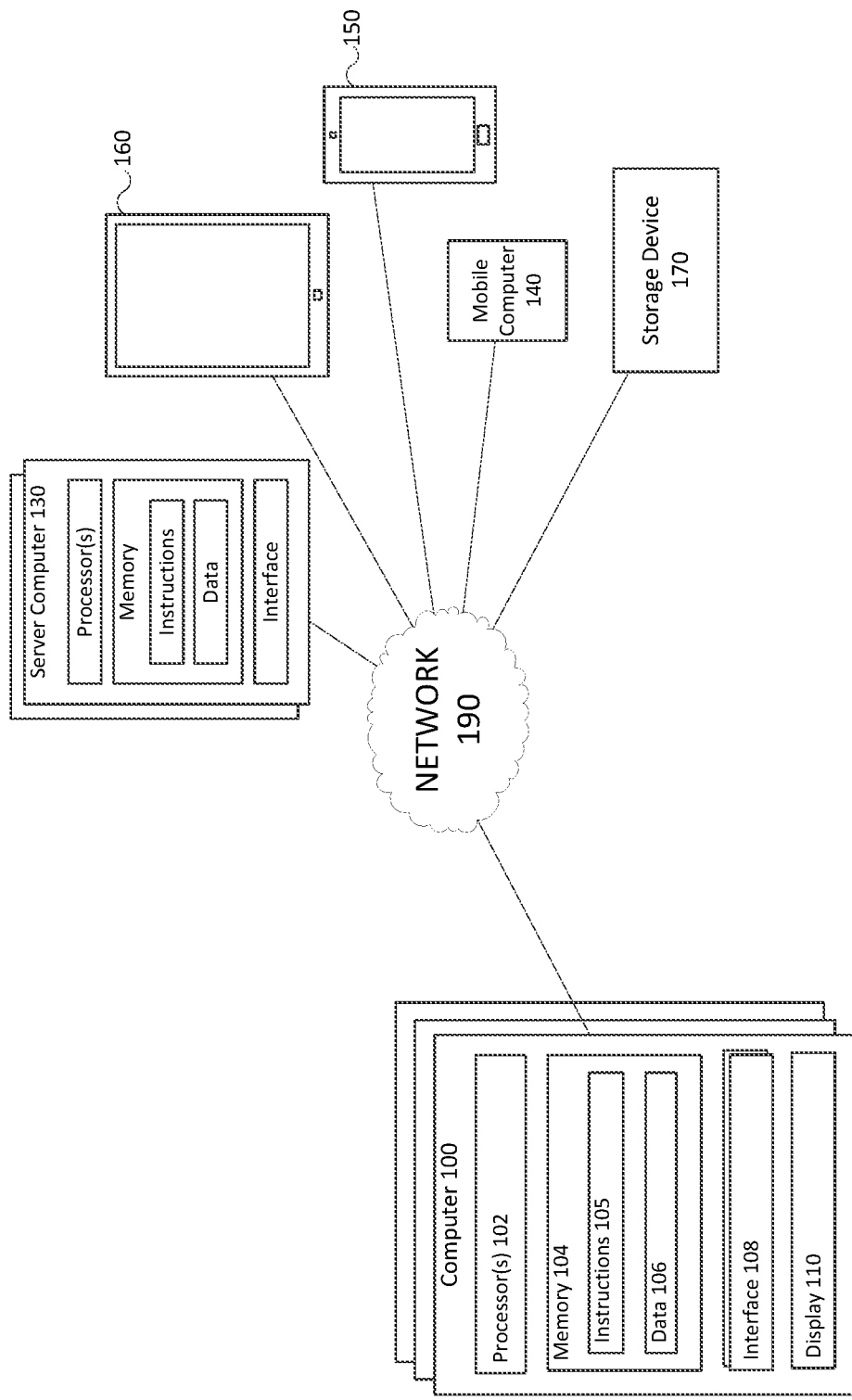
FIGS. 1 and 2 illustrate example systems in accordance with one or more aspects of the invention.

The invention relates to a system and method for control of at least one bioreactor, other cell cultivation-related equipment, and systems containing any combination of the same. For example, the system and method for bioreactor control may include controlling a plurality of bioreactors and other types of cultivation-related equipment, such as equipment for fermenting, harvesting, equipment for microfiltration and purification (e.g., liquid chromatography skid system), buffer preparation, media preparation, etc. The plurality of bioreactors and the other types of cultivation-related equipment may be located in a plant, and the control of such equipment may be known as a Plant-Wide Control System (PWCS).

As one example, the PWCS may be a control system for automated batch processing (e.g., a process that leads to the production of quantities of material, such as cells, by subjecting quantities of input materials to an ordered set of processing activities over a finite period of time using one or more pieces of equipment). The PWCS may be divided into three main components: (1) hardware (including operating systems, such as a controller communicating with one or more servers of a network associated with the PWCS); (2) software (such as a control module) for performing control; and (3) one or more instrument control loops, which may be used by the software to maintain certain process values.

In one aspect of the invention, one or more control modules may be used to perform control, such as read input and manage alarms or alarming functionalities for various field devices (e.g., sensors with transmitters, scales, switches, pumps, control valves, valves, pumps with variable frequency drives, agitators with variable frequency drives, valves with limit switches) or any type of equipment related to cell cultivation. By way of example, the control module may be software that may link various algorithms, and process certain conditions, alarms displays, and other characteristics associated with the PWCS. Moreover, control modules may allow for interface capability so that users or operators may manipulate module parameters. For instance, a graphical user interface (GUI) such as an operator interface (OI) may display certain data and processing units for an operator. An operator may manipulate and adjust module parameters from central, multiple or remote locations of operation.

The control modules may perform control via one or more control loops. For example, the control loop may include at least three components: an actuator, a sensor-transmitter, and a loop controller. In some examples, the control module may be included in the control loop. Applications related to control loops may include temperature control for bioreactors, pressure control within chromatography skids, level control for diafiltration processing, managing dissolved oxygen concentrations, other gas concentrations, control of impeller speed, control of bubble size of critical gases, etc.

As such, the systems and/or methods described in the present disclosure are capable of maintaining an optimal environment for each cell and product type mentioned above. For example, the optimal pH may be controlled at a set point that can vary (depending on a particular cell and product type combination), for instance, from 6.00 to 8.00 and controlled within 0.10 of the desired pH set point, or any other suitable ranges. Similarly, the temperature set point can vary, for instance, between 10.0 and 130.0 degree Celsius and controlled within 0.2 degree Celsius of the set point and the dissolved oxygen set point can vary, for instance, between 8.0 and 80.0 percent and controlled within 5 percent of the set point, or any other suitable ranges. In a further example with respect to a bioreactor, the purification equipment, such as the chromatography skids, need to capable of operating different combination of column sizes (varying in diameter, for instance, from 45 cm to 2000 cm with bed heights from 15 to 30 cm) containing various types of chromatography resins (such as Affinity, Ion Exchange, Hydrophobic, Hydroxyapatitie); where each combination of column and resin may require a unique flow rate and pressure combination that needs to be controlled by the systems and methods that are described in the present invention, where typically the flow rates need to be controlled at set points that can vary, for instance, from 50 L/hr to 1000 L/hr and pressures that need to be maintained below a high pressure limit of, for instance, 4 bars, or any other suitable ranges.

FIG. 1 illustrates an example system in accordance with one or more aspects of the invention. The system may include one or more computing devices, e.g., computer 100, server computer 130, mobile computer 140, smartphone device 150, tablet computer 160, and storage device 170 connected to a network 190. For example, the computer 100 may be a desktop computer, which is intended for use by one or more users. The computer 100 includes various components associated with a desktop computer, such as one or more processors 102, memory 104, e.g., permanent or flash memory (which includes instructions 105 and data 106), one or more interfaces 108, and a display 110. In a further example, similar to the computer 100, the server computer 130 may include at least one processor, memory which also includes instructions and data, one or more interfaces, and/or a display (not shown). Moreover, the mobile computing device 140 may be a laptop (or any type of computer that is portable or mobile, such as an Ultrabook) and also include components similar to the computer 100 and/or server computer 130. The computer 100 may be configured to communicate with the server computer 130, the mobile computer 140, the smartphone device 150, the tablet computer 160 and/or the storage device 170 via the network 190. As shown in FIG. 1, the cascaded blocks associated with a particular component illustrate that more than one of those components may exist, which is only an example, and it may be understood that different components can be cascaded and that there may be numerous variations thereof.

The computer 100 may include a processor 102 (e.g., controller, which will be further discussed below), which instructs the various components of computer 100 to perform tasks based on the processing of certain information, such as instructions 105 and/or data 106 stored in the memory 104. For example, the processor 102 may be hardware that can be configured to perform one or more operations, e.g., adding, subtracting, multiplying, comparing, jumping from one program to another program, operating input and output, etc., and may be any standard processor, such as a central processing unit (CPU), or may be a dedicated processor, such as an application-specific integrated circuit (ASIC) or a field programmable gate array (FPGA) or an industrial process controller. Moreover, the processor 102 may have any suitable configuration and/or configuration of circuitry that processes information and/or instructs the components of computer 100. While one processor block is shown in FIG. 1, it may be understood that the computer 100 may also include multiple processors to individually or collectively perform tasks, as described above. In one or more embodiments, the computer 100 may be an industrial controller.

Memory 104, whether permanent or flash, may be any type of hardware configured to store information accessible by the processor 102, such as instructions 105 and data 106, which can be executed, retrieved, manipulated, and/or stored by the processor 102. It may be physically contained in the computer 100 or coupled to the computer 100. For example, memory 104 may be ROM, RAM, CD-ROM, hard drive, write-capable, read-only, etc. Moreover, the instructions 105 stored in memory 104 may include any set of instructions that can be executed directly or indirectly by the processor 102. For example, the instructions 105 may be one or more "steps" associated with software that can be executed by the processor 102. The instructions 105 may be also transferred onto memory 104 in various way, e.g., from server computer 130 and/or storage device 170 via network 190. In addition, the data 106 stored in memory 104 may be retrieved, stored or modified by the processor 102, for example, in accordance with the instructions 105. In one aspect, the data 106 may be stored as a collection of data. For instance, although the invention is not limited by any particular data structure, the data 106 may be stored in registers, in a database as a table having multiple fields and records, such as an XML. The data 106 may be formatted in any computer readable format such as, but not limited to, ASCII, Extended Binary-Coded Decimal Interchange Code (EBCDIC), binary, Objectivity, SQL or other suitable database formats, etc. The data 106 may also be any information sufficient to identify the relevant data, such as text, codes, pointers, information used by one or more functions to calculate the data, etc. Similar to the instructions 105, the data 106 may also be transferred onto memory 104 from various components via network 190.

According to one aspect of the invention, the instructions 105 may include at least a set of executable instructions to read various input values from the bioreactors, related equipment, and field devices, exert control, and manage alarms, recording, reporting, communication and alarming functionalities. The instructions 105 may be associated with the various control modules for controlling the field devices and related equipment. The instructions 105 may be executable code or one or more algorithms for processing data. In that regard, and as will be further discussed in the examples below, the set of executable instructions may be considered the "back-bone" of the control module for performing control on one or more bioreactors and related cell cultivation-related equipment, and may be configured to link algorithms, processing conditions, alarms, displays, and other characteristics.

According to another aspect of the invention, the data 106 may include data that may be used by the control module, such as sensor readings, data collected by sensors, predetermined parameters, readings associated with valves, pumps, agitators, scales and switches, user defined target values at which a process value is to be maintained by the PWCS ("setpoint"), temperature measurements, pressure measurements, level measurements, dissolved oxygen measurements, etc.

Interface 108 may be a particular device (such as a field-mounted instrument, processor-to-processor communication, keyboard, mouse, touch sensitive screen, camera, microphone, etc.), a connection or port that allows the reception of information and data, such as interactions from a user or information/data from various components via network 190. For instance, the interface 122 may include one or more input/output ports. The input/output ports may include any suitable type of data port, such as a digital control bus (Foundation™, ProfitbusDP™, DeviceNet™, Modbus IEEE RS-485, Modbus/IP, Serial IEEE RS-232, universal serial bus (USB) drive, zip drive, card reader, CD drive, DVD drive, etc.

The display 110 may be any suitable type of device capable of communicating data to a user. For example, the display 110 may be a liquid-crystal display (LCD) screen, a light emitting diode (LED) screen, a plasma screen, etc. The display 110 may provide to the user various types of information, such as visual representations of the software that can be executed by the computer 100 and various data, and the like, associated therewith.

Figure 11A:
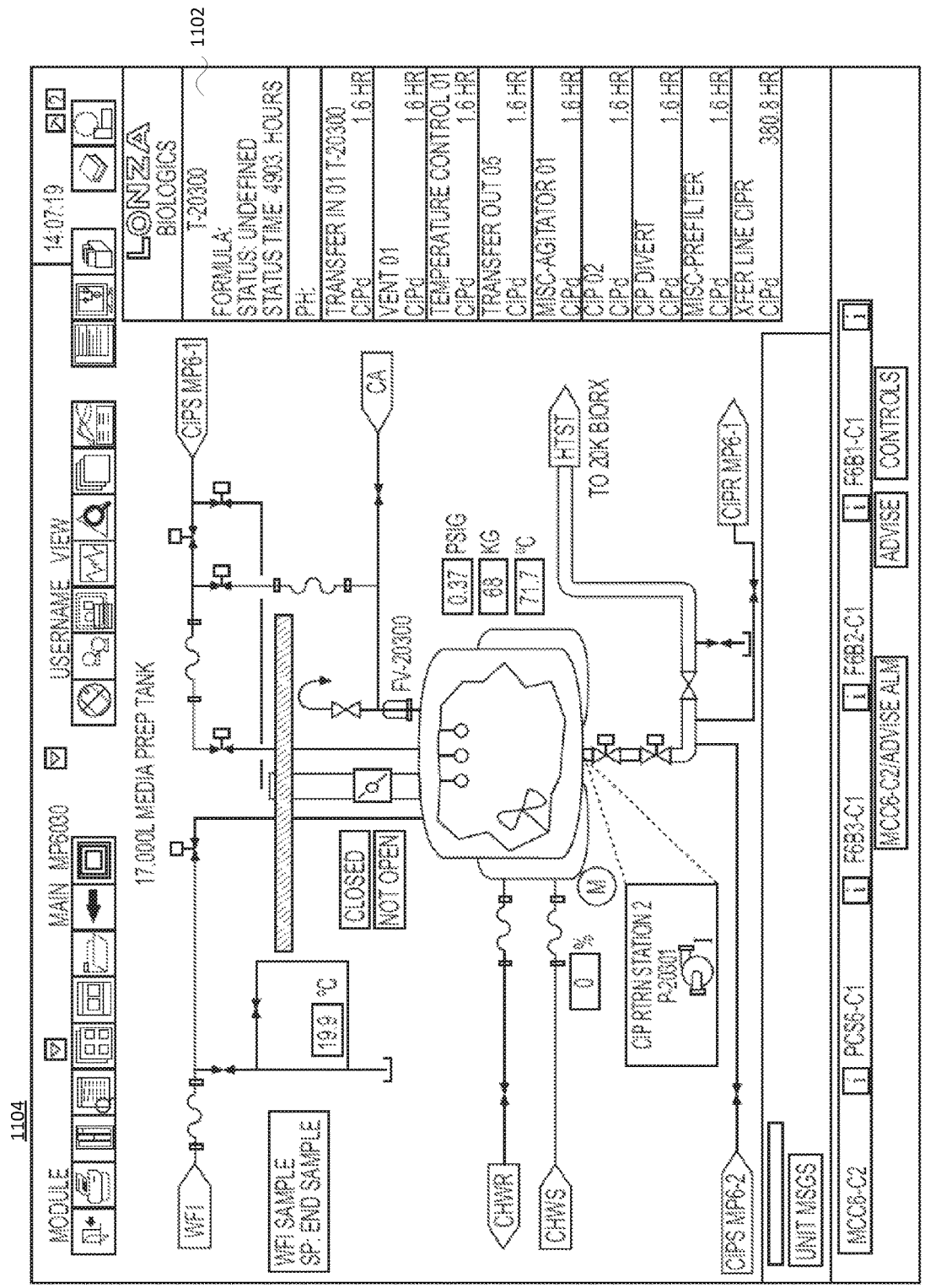
FIG. 11A illustrates an example operator interface in accordance with one or more aspects of the invention.
Figure 11B:
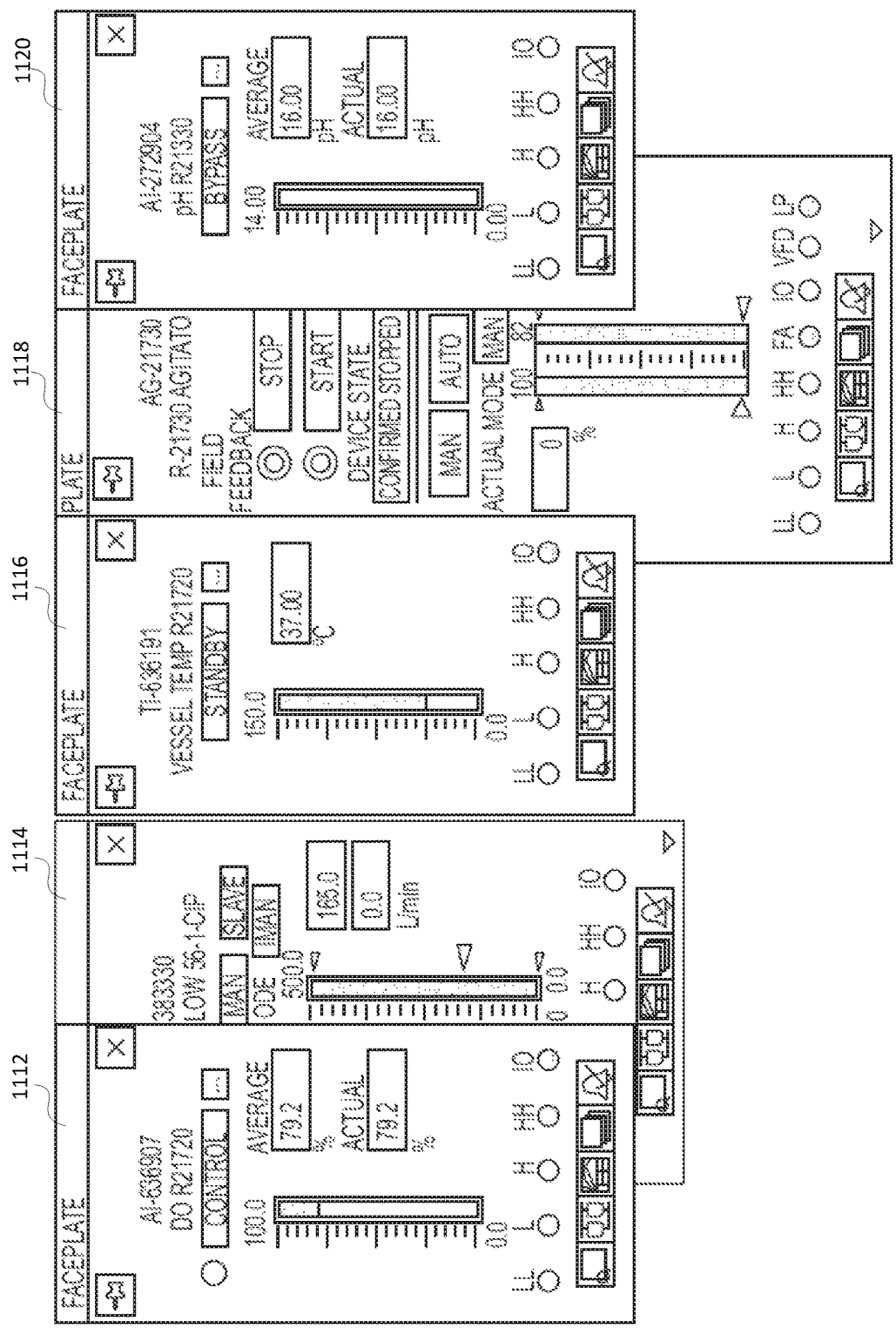
FIG. 11B illustrates example faceplates associated with an operator interface in accordance with one or more aspects of the invention.

According to one aspect, a user may input information and/or data using the interface 108. The interface 108 may be a graphical user interface (GUI) that is displayed to the user/operator on the display 110. By way of example only, the GUI may be an operator interface (OI) that displays processing units and data to a user/operator. For instance, FIGS. 11A and 11B are examples of an OI and associated functionalities, which will be further described below with respect to the discussion of the control module functionalities of the present invention.

The server computer 130 may be rack mounted on a network equipment rack and/or located in a data center. In some examples, via the network 190, the server computer 130 may serve various requests associated with the programs executed on the computer 100, mobile computer 140, the smartphone device 150, the tablet computer 160, and/or the storage device 170. In further examples, the server computer 130 may be part of a plurality of server computers that support a back-end system (which may be "invisible" to users).

Mobile or portable computing devices, such as the mobile computer 140, the smartphone device 150, and tablet computer 160, may include similar components and functions to the computer 100 and/or server computer 130, e.g., one or more processors, memory, input/output capabilities, display, etc. and, by common Thin Client and Remote Desktop protocols, access display 110 and interface 108 present on the computer 100.

For example, the mobile computer 140 may be any type of device that is mobile or portable with computing capability and connectivity to a network. For example, the mobile computer 140 may be a laptop, an Ultrabook, smartphone, PDA, tablet computer, a wearable computing device, etc. The mobile computer 140 may also have one or more processors, memory, user interfaces, wired or wireless network connection hardware, and other types of components associated with a mobile computing device. Thus, the mobile computer 140 may be able to connect to network 190 via a wired or a wireless connection and communicate with other components connected to the network 190, such as server computer 130, storage device 170, etc.

The smartphone device 150 may be a mobile cellular phone with computing capability and network connectivity. For example, the smartphone 150 may include one or more processors, memory, one or more user interfaces, such as a QWERTY keypad, a camera, image sensors, a global positioning system (GPS), accelerator, temperature sensors, etc. Similar to the computer 100 and the server computer 130, the smartphone device 150 may be configured to execute computer instructions, applications, programs, and any set of instructions and data. Moreover, the tablet computer 160 may also include one or more processors (configured to execute computer instructions and/or applications), memory, one or more interfaces, a touchscreen display, sensors, microphone, camera, speakers, networking hardware (configured to connect to a network, such as network 190, via a wired or wireless connection), etc.

The storage device 170 may be configured to store a large quantity of data and may also be configured to transfer such data when requested or accessed by other components of network 190. For example, the storage device 170 may be a collection of storage components, such as ROM, RAM, hard-drives, solid-state drives, removable drives, network storage, virtual memory, multi-leveled cache, registers, CD, DVD, etc. In addition, the storage device 170 may be configured so other components of network 190, such as the computer 100 and/or server computer 130, can access and provide data to other components connected to the network 190.

In one embodiment, the storage device 170 may store the above-described data associated with data 106, such as data that may be used by the control module, such as sensor readings, data collected by sensors, predetermined parameters (e.g., can be downloaded to controllers and referenced by other outside systems and/or users), valve, pump, agitator, scales and switch readings, user defined target values, or setpoints, at which a process value is to be maintained by the PWCS, temperature measurements, pressure measurements, level measurements, dissolved oxygen measurements, and the like. In another example, the storage device 170 may be updated to add new data. If the operator, for example, defines a new predetermined value for an alarm function, then the old predetermined value may be updated to reflect the new predetermined value.

The network 190 may be any suitable type of network, wired or wireless, configured to facilitate the transmission of data, instructions, etc. between one or more components of the network. For example, the network 190 may be a local area network (LAN) (e.g., Ethernet or other IEEE 802.03 LAN technologies), Wi-Fi (e.g., IEEE 802.11 standards), wide area network (WAN), virtual private network (VPN), global area network (GAN), or any combinations thereof. In this regard, the computer 100, server computer 130, mobile computer 140, smartphone device 150, and/or tablet computer 160 may connect to and communicate with one another via the network 190.

While the computer 100 may be a desktop computer in the above-described examples, computer 100 is not limited to just desktop computers, and any of the computers illustrated in FIG. 1 may be any device capable of processing data and/or instructions and transmitting and/or receiving data. Moreover, it will be understood by those of ordinary skill in the art that those components may actually include multiple processors, memories, instructions, data or displays that may or may not be stored within the same physical housing. For example, some or all of the instructions 105 and data 106 may be stored on removable media, or may be stored in a location physically remote from, yet still accessible by, the processor 102. And although the various components of FIG. 1 are connected to the network 190, it may be understood that the components may also be connected to each other, in any suitable combination.

Figure 2:
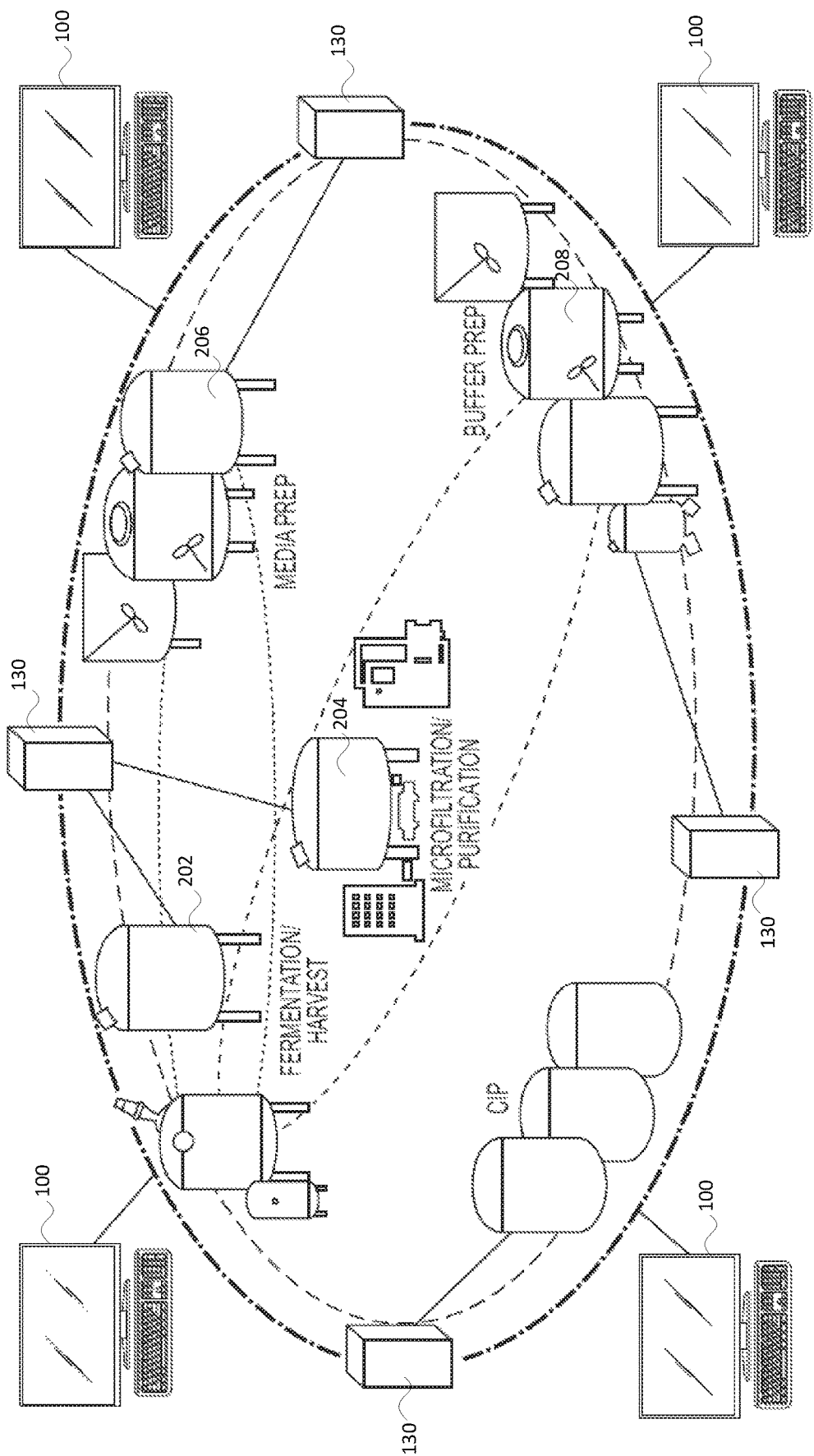

FIG. 2 illustrates another example system in accordance with aspects of the invention. In this example, the system represents a PWCS, and the various components depicted in FIG. 1, may be configured in such a manner to facilitate the control of the bioreactors and related equipment, such as equipment 202 for fermentation and/or harvest, equipment 204 for microfiltration and purification (e.g., chromatography skid), equipment 206 for media preparation, such as Clean In Place (CIP) systems and System In Place (SIP) systems, equipment 208 for buffer preparation, and various field devices (e.g., sensors with transmitters, scales, switches, pumps, control valves, discrete valves, pumps with fixed-speed starters or variable frequency drives, agitators with variable frequency drives, discrete valves with limit switches). One or more computers, such as computer 100 of FIG. 1, may be dispersed throughout the system and each computer may be dedicated to certain control and/or portions of the depicted system. Similarly, server computers, such as server computer 130 of FIG. 1, may also be physical or virtual and dispersed throughout the system and dedicated to certain portions of the system to facilitate the communication of data and instructions.

Figure 3:
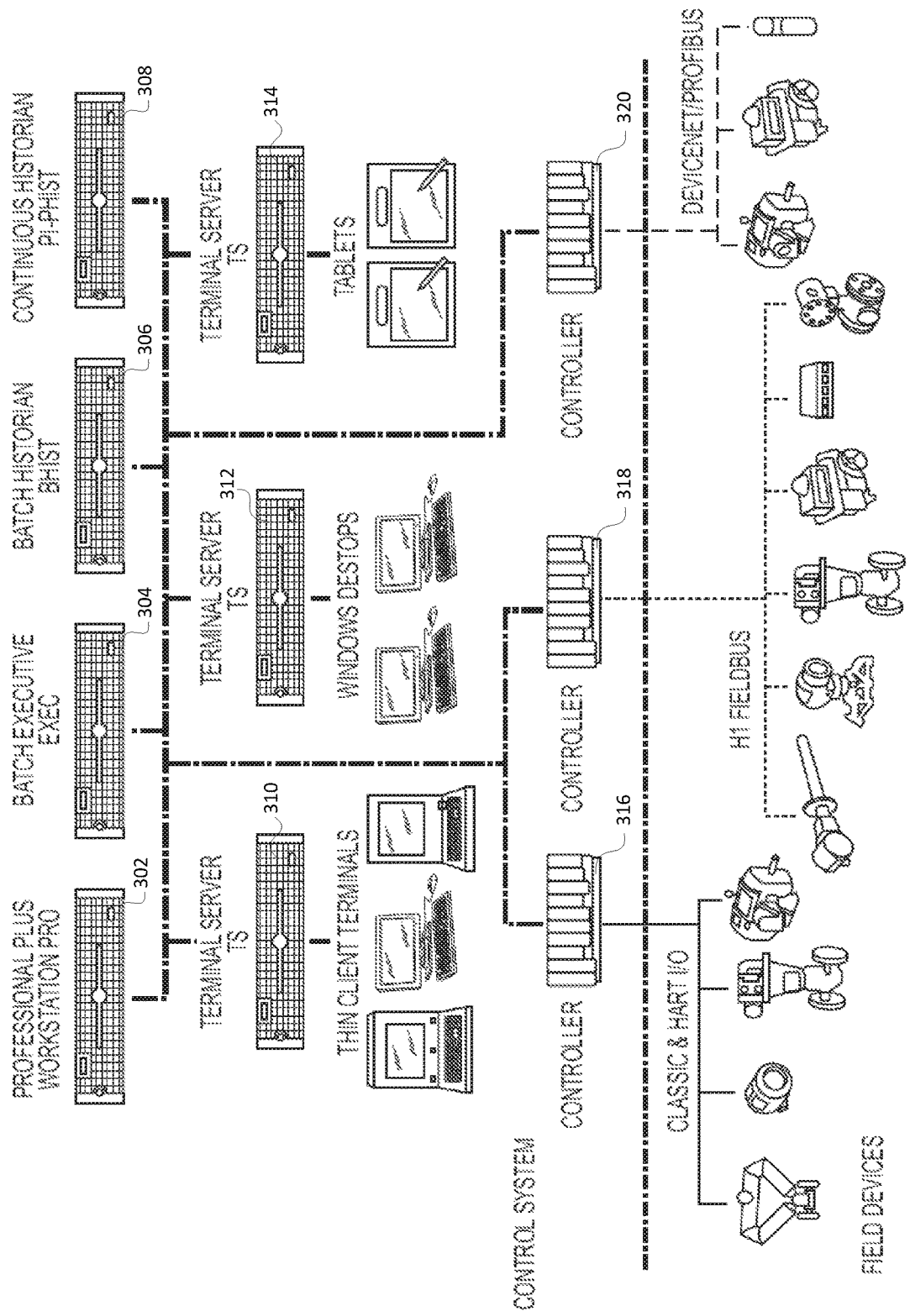
FIGS. 3 and 4 illustrate diagrams of system components in accordance with one or more aspects of the invention.

FIG. 3 illustrates a diagram, for example, of the system shown in FIG. 2 in accordance with aspects of the invention. As shown in FIG. 3, the Professional Plus Workstation (PRO) 302 may be a central database for the PWCS, the Batch Executive (EXEC) 304 stores, for instance, recipe information and may control batch processing, the Batch Historian (BHIST) 306 records and stores batch-related data from the PWCS, the Continuous Historian (PI-PHIST) 308 records and stores continuous plant data from the PWCS, each of the Terminal Servers (TS) 310, 312, and 314 may be a host for remote access sessions for thin client terminals, such as desktop computers and tablet computers, and each of the controllers 316, 318, and 320 is a PWCS device that may execute and run algorithms and/or set of executable instructions used to control the processing equipment and functionalities. Any one of the illustrated components in FIG. 3 may be (or correspond to) one or more of the computer 100, server computer 130, mobile computer 140, smartphone device 150, tablet computer 160, and/or the storage device 170.

Figure 4:
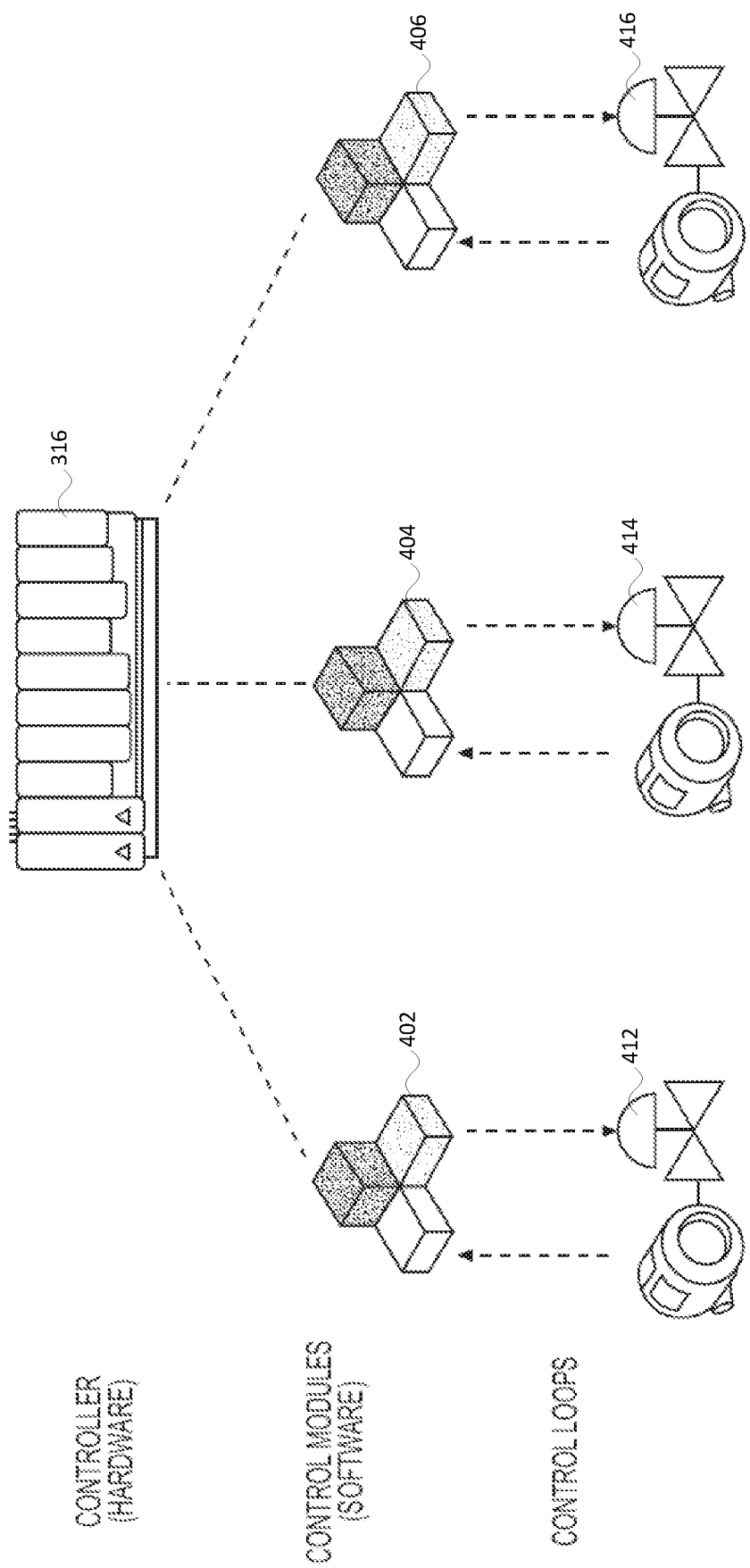

The controllers 316, 318, and 320, which may be hardware, implement one or more control modules, which may be software, to control one or more control loops, which control the various field devices shown in FIG. 3, via the control modules. The control module may be part of the control loop or may be external to the control loop in accordance with aspects of the present disclosure. This is illustrated by the example diagram in FIG. 4. FIG. 4 shows a controller, for example, controller 316, associated with three different control modules 402, 404, and 406, each of which is associated with a respective control loop. By way of example, control module 402 is associated with control loop 412, control module 404 is associated with control loop 414, and control module 406 is associated with control loop 416. As an example, the algorithms that are run on the controller 316 may be used in the control loops, batch control and continuous control functionalities. The control modules 402, 404, 406 may also be configured to drive individual elements that are not associated with a particular control loops, such as driving a value open or reading from a pressure transmitter. Moreover, the controller 416 may communicate processing data to one or more system servers, as shown in FIGS. 1 and 3. The controllers 316, 318, 320 and other controllers, for instance, may also be physically dispersed throughout a particular plant for bioreactor control.

Further to the system and operations thereof described above and illustrated in FIG. 1, various operations will now be described below. The following operations are not required to be performed in a particular or precise order. Rather, the various steps may be performed in any suitable order, and different combinations, or simultaneously, one or more steps may also be added or omitted. The "recipe" configuration, for example, which may contain the parameters to define the sequential orchestration and control loop setpoints, required to produce unique products using the same hardware/software/configuration, determines how and when the related control loops are applied. Various examples and aspects of a control loop and a corresponding control module will be discussed in further detail below.

Figure 5:
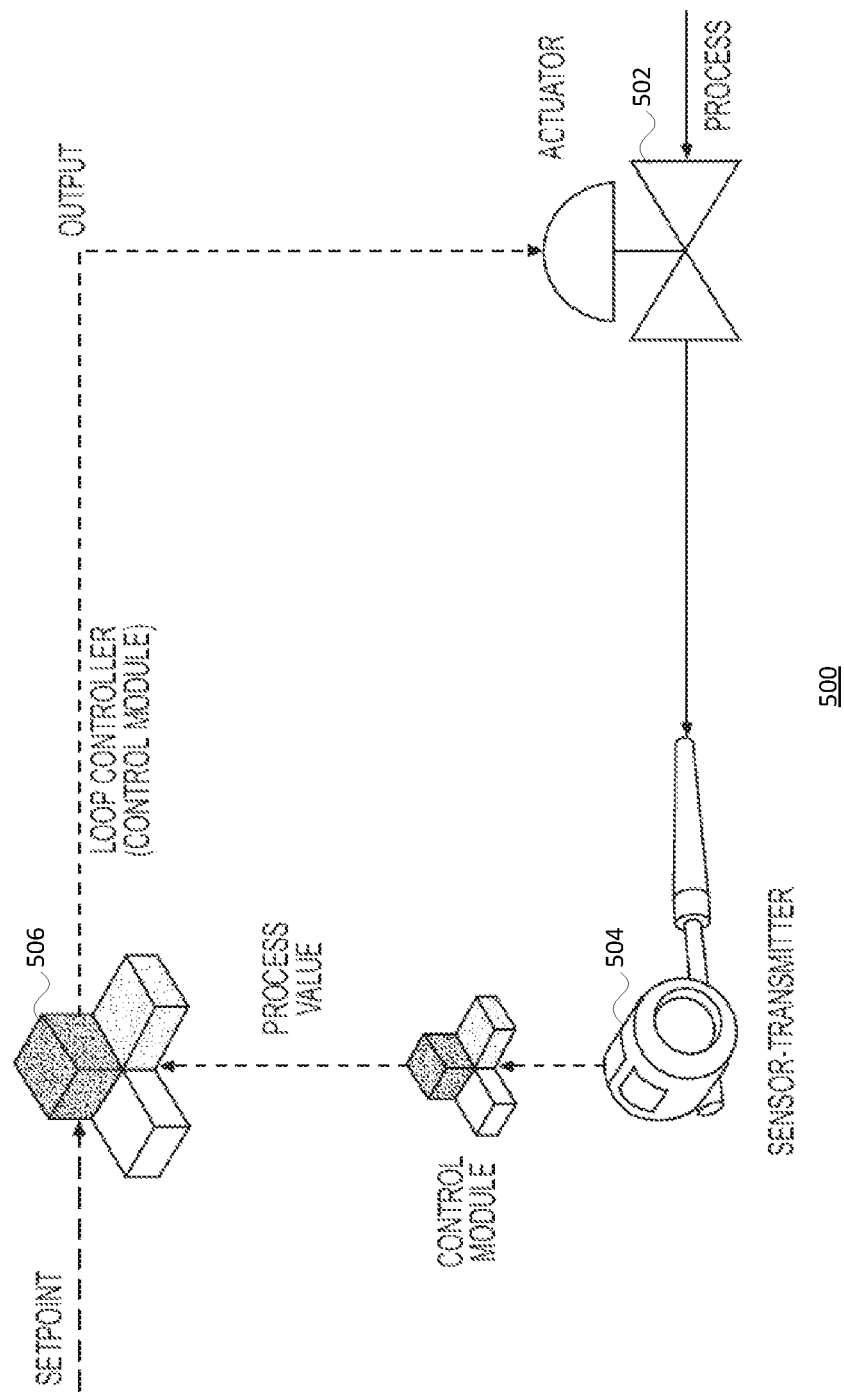
FIG. 5 illustrates a control loop in accordance with one or more aspects of the invention.

FIG. 5 illustrates a control loop 500 in accordance with aspects of the present disclosure that has at least three components: an actuator 502, a sensor-transmitter 504, and a loop controller 506. Control loops may have many possible configurations and many other configurations with sequential phase logic to run multiple products for various end-users according to their respective needs with the same logic. In some instances, as shown in FIG. 5, the loop controller 506 may be implemented by one or more control modules (as will be further described below), such as the control modules 402, 404, and 406 shown in FIG. 4, to control the loop.

The actuator 502, for example, may be a physical device that is manipulated and/or controlled by the loop controller to regulate a process value (e.g., a value that is read and/or processed from a field device). Some examples of actuators include control valves, pumps, agitators, and the like. The sensor-transmitter 504 may be a physical device that is configured to read and/or process certain values and transmit input to the loop controller. Some examples of process values may include temperature, pressure, pH, flow, dissolved oxygen, conductivity, level, etc. Moreover, the loop controller 506, as set forth above, may be the "brains" of the control loop. The loop controller 506 can be one or more software control modules that can adjust the control loop in accordance with and based on programmed algorithms and/or sets of executable instructions. In some instances, as described above, hardware controllers may contain multiple control module algorithms and configurations associated with certain control loops.

Figure 6:
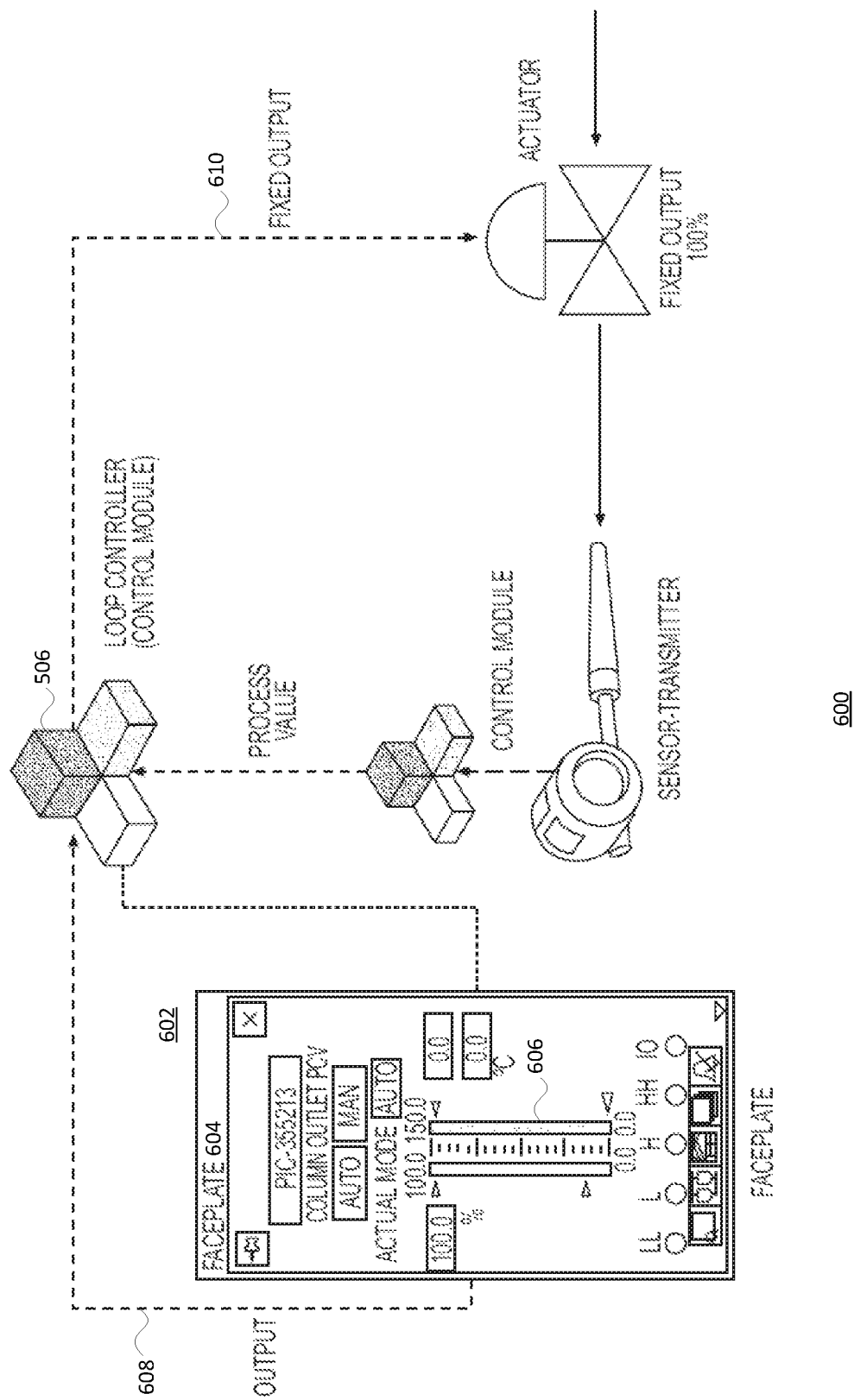
FIG. 6 illustrates a control loop operating in manual mode in accordance with one or more aspects of the invention.
Figure 7:
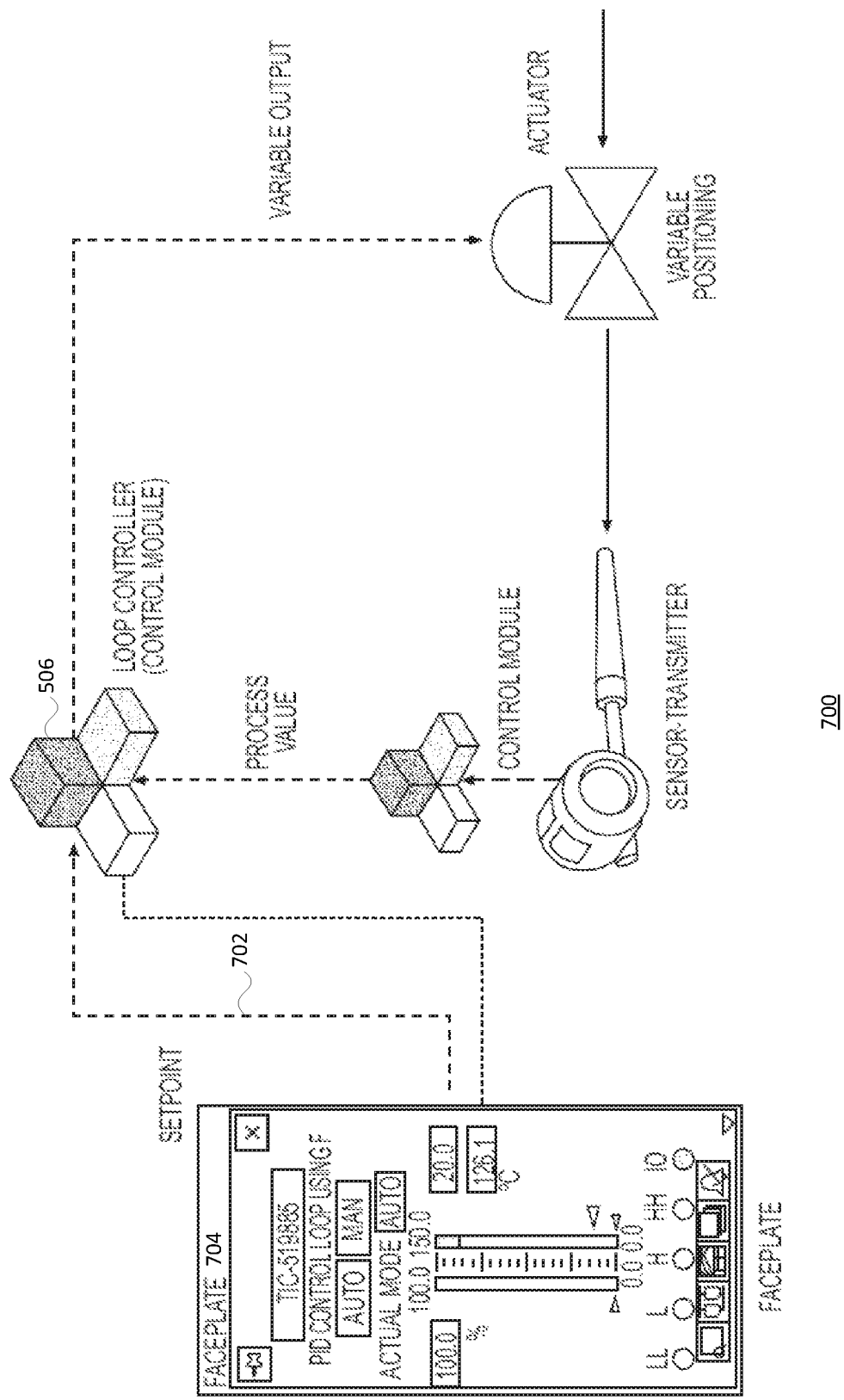
FIG. 7 illustrates a control loop operating in an automatic mode in accordance with one or more aspects of the invention.
Figure 8:
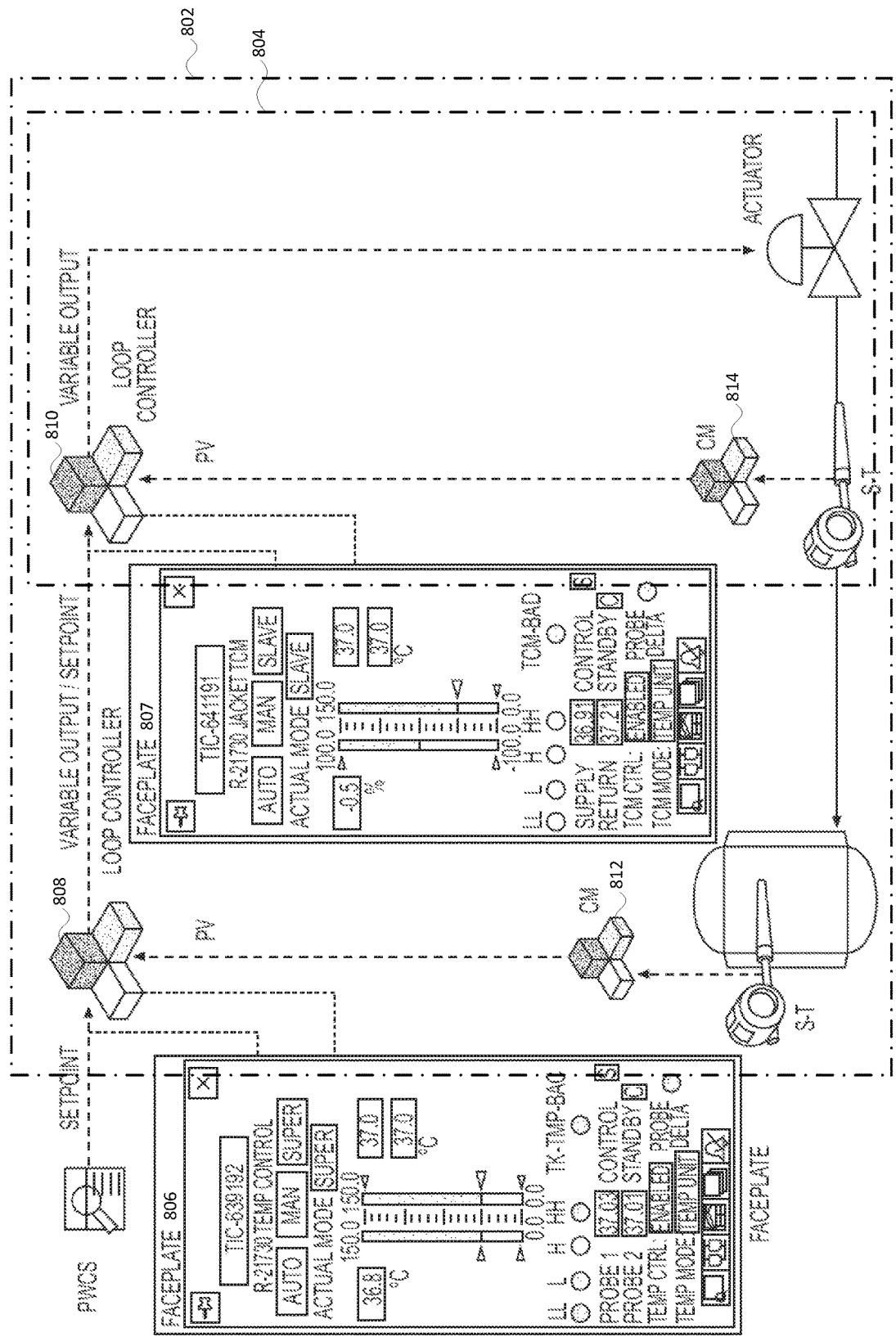
FIG. 8 illustrates a control loop operating in a cascade mode in accordance with one or more aspects of the invention.

The control loop 500, illustrated in FIG. 5, may be implemented in different operating modes, such as manual, automatic, cascade (supervisory), and cascade (slave), each of which will be described below. FIGS. 6-8 illustrate the different operating modes.

Control Loop Operating in Manual Mode

FIG. 6 illustrates the control loop 500 operating in manual mode 600 in accordance with one or more aspects of the invention. For example, a user or an operator may manipulate the output of the control loop 500 when permitted by control logic, such as the operator interface (OI) 602. In FIG. 6, the OI 602 is a "faceplate" 604. In this instance, a slide bar 606 on the "faceplate" 604 of the OI 602 is adjusted by numerical entry to "100.0." The output 608 is transmitted to the loop controller 506 (e.g., the control module), and then the fixed output 610 is transmitted to the actuator 502. The actuator 502 performs the fixed output of 100 percent, which is read by the sensor-transmitter 504, and then by way of a control module (e.g., a second control module), the process value (e.g., the value that is read by the sensor) is transmitted back to the loop controller 506 and displayed on the faceplate for the user/operator.

Control Loop Operating in Automatic Mode

FIG. 7 illustrates the control loop 500 operating in automatic mode 700 in accordance with one or more aspects of the invention. For example, a user or operator may enter or input a setpoint 702 using the control loop faceplate 704, and from there, the loop controls, automatically or dynamically, to that user-input setpoint. As noted above, the setpoint 702 may be a target value at which a process value is to be maintained by the PWCS. Here, the setpoint 702 is entered and fed into the loop controller 506 (e.g., a control module), where a variable output from the loop controller is transmitted to the actuator 502. The actuator 502 then performs variable positioning and the sensor-transmitter 504 reads an associated value and then the read value is transmitted to a control module (e.g., a second control module) which generates a process value, then the process value is transmitted back to the loop controller 506. In one example, it is determined whether the read process value is equivalent to or matches the setpoint (e.g., target value). If the process value and the setpoint value do not match, then the control loop 500 may automatically or dynamically adjusts until the process value matches that user-input setpoint. The process value output may be displayed on the faceplate 704 for the user/operator.

Control Loop(s) Operating in Cascade Mode

FIG. 8 illustrates a control loop 800 operating in cascade mode in accordance with one or more aspects of the invention. For example, two or more loops, such as a supervisory "master" loop 802 and a secondary "slave" loop 804, may be cascaded. In this example, the supervisory loop 802 receives and controls to an inputted setpoint from the PWCS control logic, such as faceplates 806 and 807, and the secondary loop 804 functions based on the outputs from the master/supervisory loop 802. As shown, two loop controllers 808 and 810 are used with two associated control modules 812 and 814. The smaller outermost loop including the actuator and the right-most loop controller is the secondary loop or slave loop 804, and the bigger overall loop including the both loop controllers 808 and 810 is the supervisory or master loop 802.

In some examples of the aspects described above, "critical" processing may require a plurality of sensors, some of which may be redundant. For example, redundant sensors may be necessary for culture growth in a bioreactor. In a further example, two sensors may be used to monitor certain process values, such as pH, temperature, and dissolved oxygen.

Figure 9:
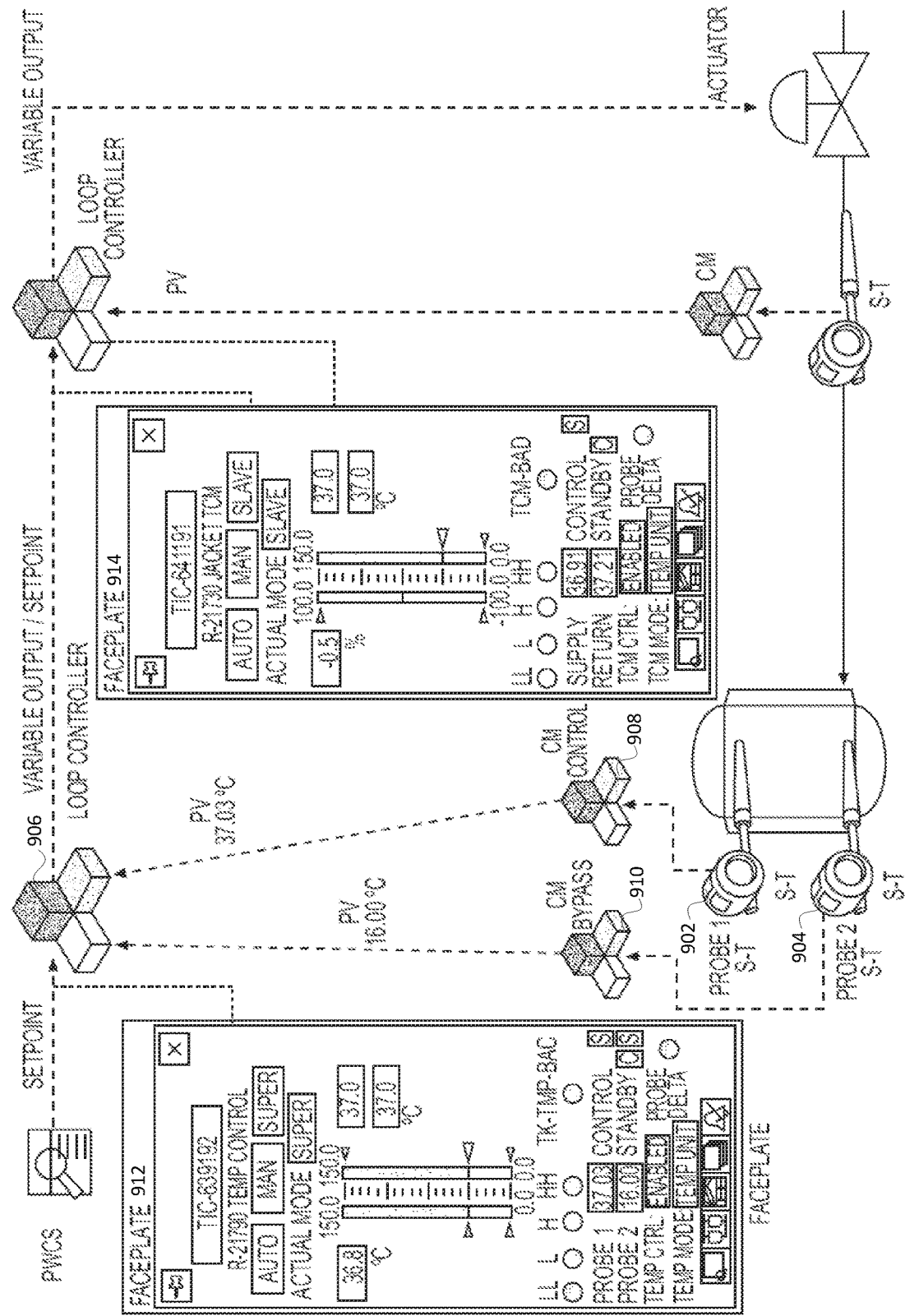
FIG. 9 illustrates a cascade loop for bioreactor temperature control in accordance with one or more aspects of the invention.

FIG. 9 is an example cascade loop 900 for bioreactor temperature control with sensor standby and bypass functionalities. For example, output from the sensors ("probe 1" 902 and "probe 2" 904) influence the cascade control loop—both the supervisory and slave loops. Those outputs are fed into a loop controller 906. Either one of the control modules 908 and 910 associated with the probes can be in "standby" mode, which represents that the control module 908 or 910 is available to be used in place of the control module actually in control. However, in "bypass" mode, the output of the sensor is not used to influence the control loop (e.g., an indication that this particular sensor should not be used to the user). These modes are displayed to the user/operator on the OI faceplates 912 and 914. These different modes of execution are further discussed below with respect to the discussion of control modules.

As described above, a control module, such as the control modules 402, 404, and 406 illustrated in FIG. 4, may be software (e.g., a set of executable instructions), which can link various algorithms, processing conditions, alarms, displays, and other characteristics. In this regard, the control module is known as a "control entity." The control modules read inputs, perform control, manage alarms associated with field devices, etc. In one example, a control module is considered to be the lowest level grouping of equipment to carry out control, such as basic control. Moreover, control modules may have interfaces, such as an OI, or any type of GUI, that allow users or operators to manipulate (e.g., input, change, update, etc.) module parameters and other types of data. It may be understood that the field devices, such as all automated field devices, may be associated with a particular control module or a set of control modules so that the field devices may be controlled and/or the associated control module(s) receive data from the field devices. For example, field devices such as valves (automated and control), pumps, agitators, sensors-transmitters, scales, and switches may be associated with the one or more control modules, as described above.

Control modules, in one or more aspects of the invention, may have different modes of execution for particular field devices, which may influence how data from the field devices are communicated. In one example, control modules for sensors in a redundant pair have "control," "standby," and "bypass" operating modes. In the control operating mode, the output from the sensors influences a cascade control loop, both the supervisory and slave loops in the cascade. In standby operating mode, the control module associated with the sensor(s) is available to be used in place of the one actually in control. In bypass operating mode, the output from the sensor(s) may be ignored by the control module. Moreover, there may be other types of modes of execution for automated valves, pumps and agitators, such as "simulate" mode (e.g., control module output does not update, but the device feedback follows the setpoint), "interlocked" mode (e.g., device is locked out by the user/operator to ensure the PWCS does not change the state of the control module), and "bypass" mode (e.g., the control module ignores field feedback, such as limit switches, but may continue to control equipment). The control module for these devices used in control loops may also be in the automatic, manual, cascade (supervisory or slave) operating modes. Moreover, for devices such as switches, scales and sensors, there also may be a simulate mode where the control module input is set by the user/operator, to which the PWCS will respond as if the input were from the respective field instrument. For these devices, the control module used in the control loops may also be in the control, standby, or bypass modes.

Figure 10:
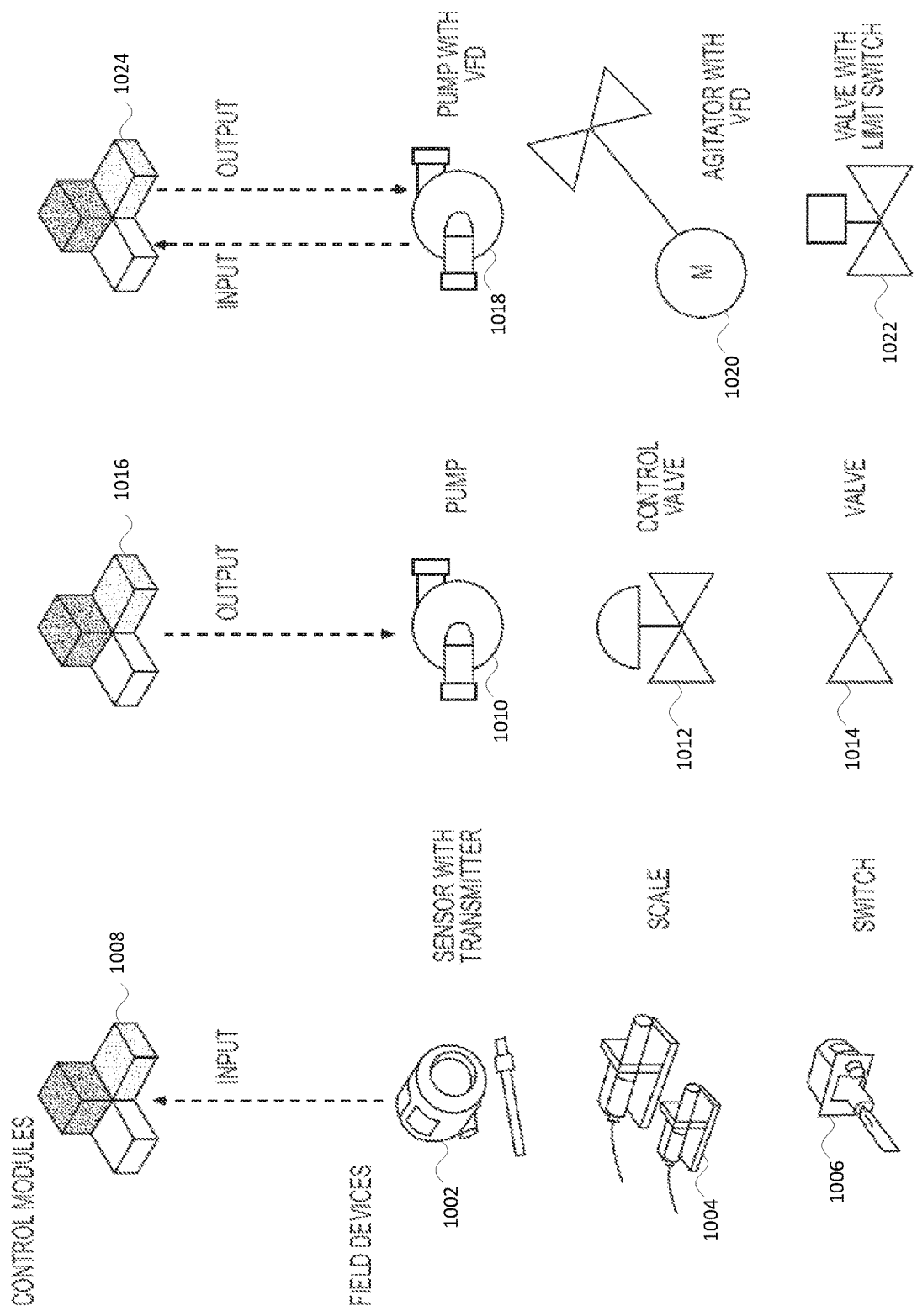
FIG. 10 illustrates input-output configurations for control modules in accordance with one or more aspects of the invention.

FIG. 10 illustrates data communication between control modules and respective field devices and further illustrates the input-output configurations of the control modules. As shown, certain field devices, such as a sensor-transmitter 1002, a scale 1004, and a switch 1006 transmit data (e.g., "input" signals) to control module 1008. In other words, in this example, the control module 1008 does not control these particular field devices; rather, it is configured to just receive data. Moreover, other field devices, such as a pump 1010, control valve 1012, and a valve 1014 without limit a switch may receive "output" signals from control module 1016. Here, for example, the control module 1016 would control these field devices. Moreover, FIG. 10 shows that certain other field devices, such as a pump 1018 with a variable frequency drive (VFD) and an agitator 1020 with a VFD, and a valve 1022 with a limit switch, which may receive output signals from control module 1024 and also transit data and/or input signals to the control module 1024. In this example, these field devices may not controlled by the control module 1024, but they may transmit "field feedback" to the control module 1024.

Limit switches may be sensors that detect the presence and absence of an object. In the PWCS, these limit switches may be used to confirm "closed" positions of valves. In some examples, limit switches are configured to transmit input signals to control modules from valves that only receive output, thus providing field feedback to the control modules.

As described above, a control module may have an interface, such as an OI, or any type of GUI, that allow users or operators to manipulate (e.g., input, change, update, etc.) module parameters and other types of data. FIGS. 11A and 11B illustrate an example operator interface and example faceplates, respectively, in accordance with aspects of the present invention.

FIG. 11A illustrates an OI displaying a visual representation of a "17,000 L MEDIA PREP TANK." As shown, there are various symbols to represent the components and field devices associated with the media prep tank, the graphics of which may change in real-time as parameters change. Icon 1102 includes various data associated with the tank is displayed, such as the "formula," "status," "status time," "pH," etc. Further illustrated are various icons 1104 associated with different functionalities, such as viewing and analyzing data, printing, etc., and are also selectable. In other examples, the user or operator may have access to a "Batch Operator Interface" or "BOI" (not shown), where the user or operator can input recipes and track the status of various types of batch processing and the like. The interface for BOI may be configured in a similar manner to the OI illustrated in FIG. 11A, or alternatively, may be more text-based, where the text is displayed on the main graphical interface display and the operator can "add," "stop" "continue," etc. batch processes using buttons or icons.

FIG. 11B illustrates example faceplates that may be associated with an OI. For example, the faceplates may be control module faceplates 1112, 1114, 1116, 1118, and 1120 include, but are not limited to, a detail display button/icon that opens module detail display, a primary control display button/icon that opens a graphic on which the module is located, a processor history view button/icon that allows the user/operator to view historical data related to the module, a control studio button/icon that opens the module, and an acknowledge alarm button/icon that acknowledges active alarms related to the module.

Other types of control module faceplates may manipulate control loops. For example, they may include, but are not limited to, a control loop mode button/icon that determines the mode in which the control loop is operating (e.g., automatic, manual, supervisory, slave), a setpoint entry field/slider/icon that allows users to adjust the control loop's setpoint in the automatic mode, a process value icon/display that displays values from the control loop's input device in engineering units, and an output entry field/slider/icon that displays values sent to the output device in percentage when in automatic mode and can be manually adjusted when the control loop is in manual mode. Faceplates may have different background colors to specify certain types of information, such as designating the plant area in which the control module's field device is located.

It may be understood by persons of ordinary skill in the art that many suitable combinations and variations of the OI, including the examples shown in FIGS. 11A and 11B, may exist and be implemented.

Figure 12A:
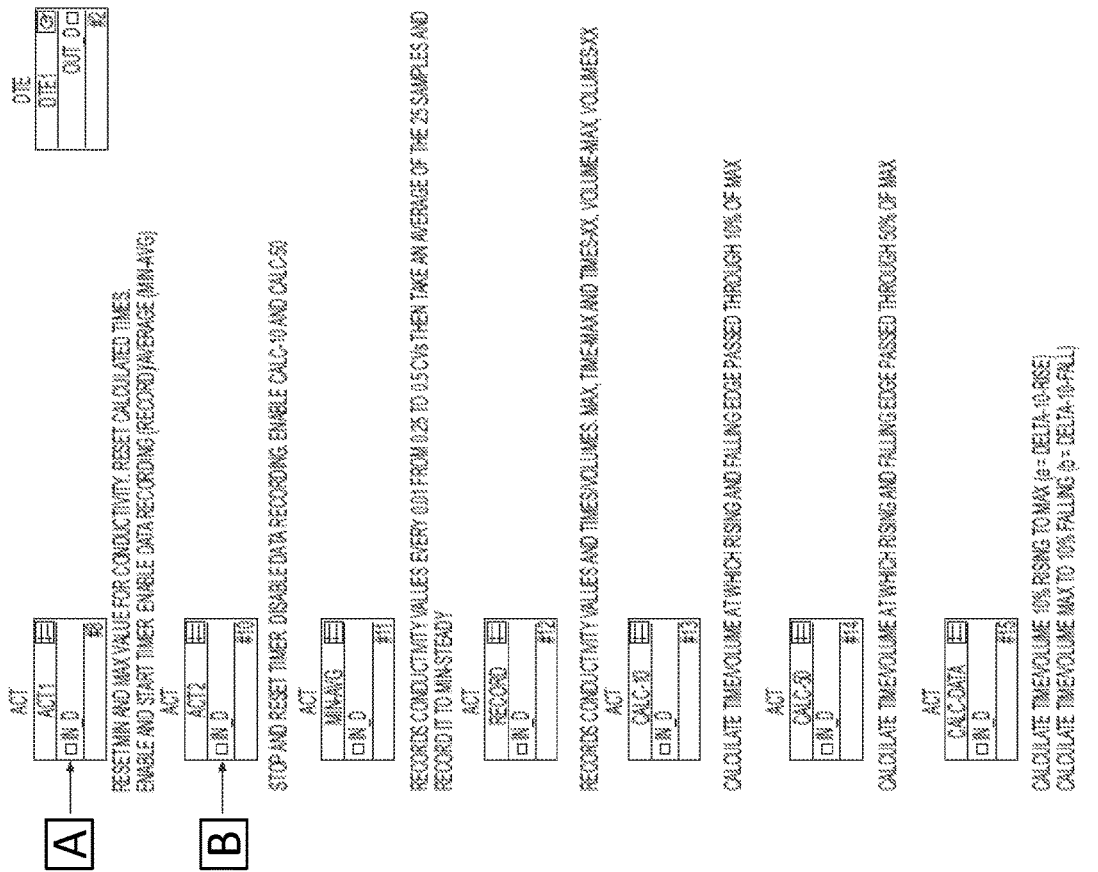
FIGS. 12A and 12B illustrate one or more control modules for handling chromatography skid calculations in accordance with one or more aspects of the invention.
Figure 12B:
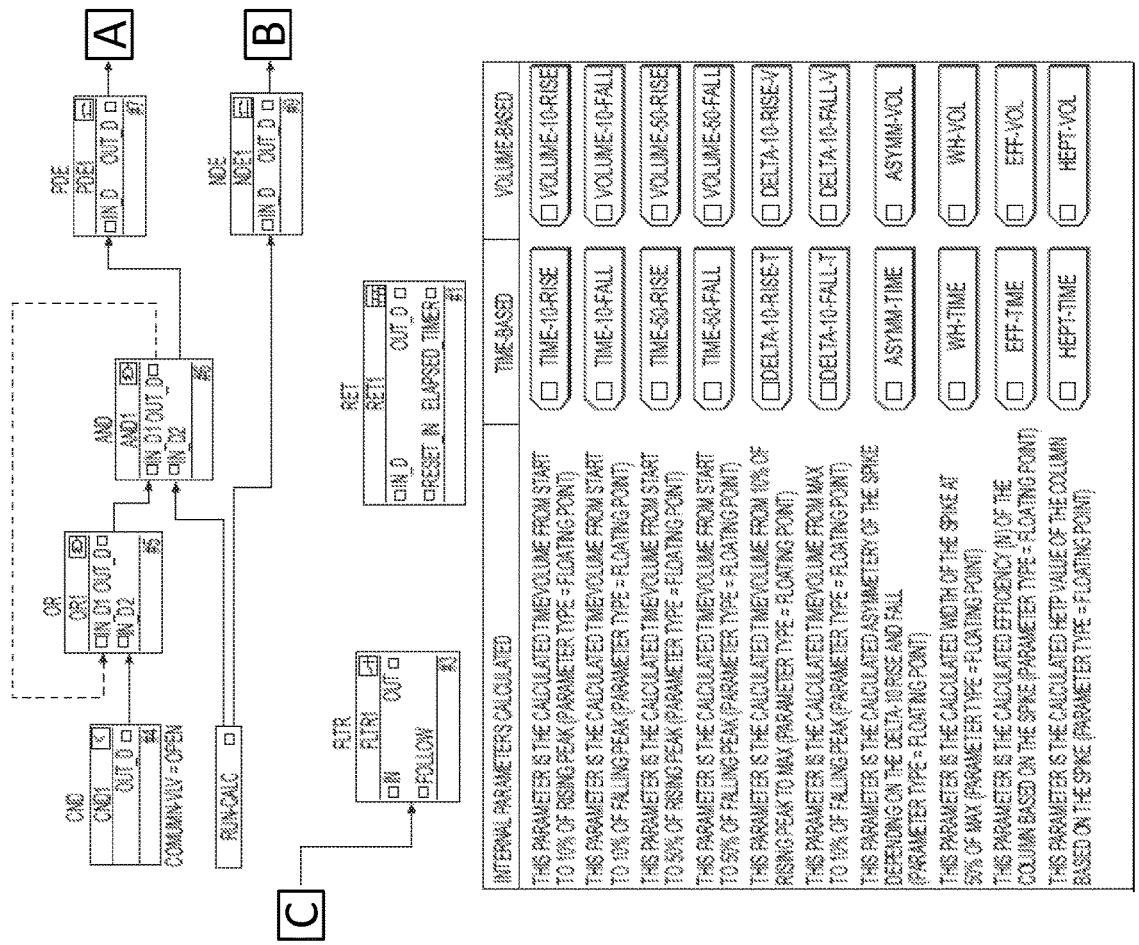
Figure 13:
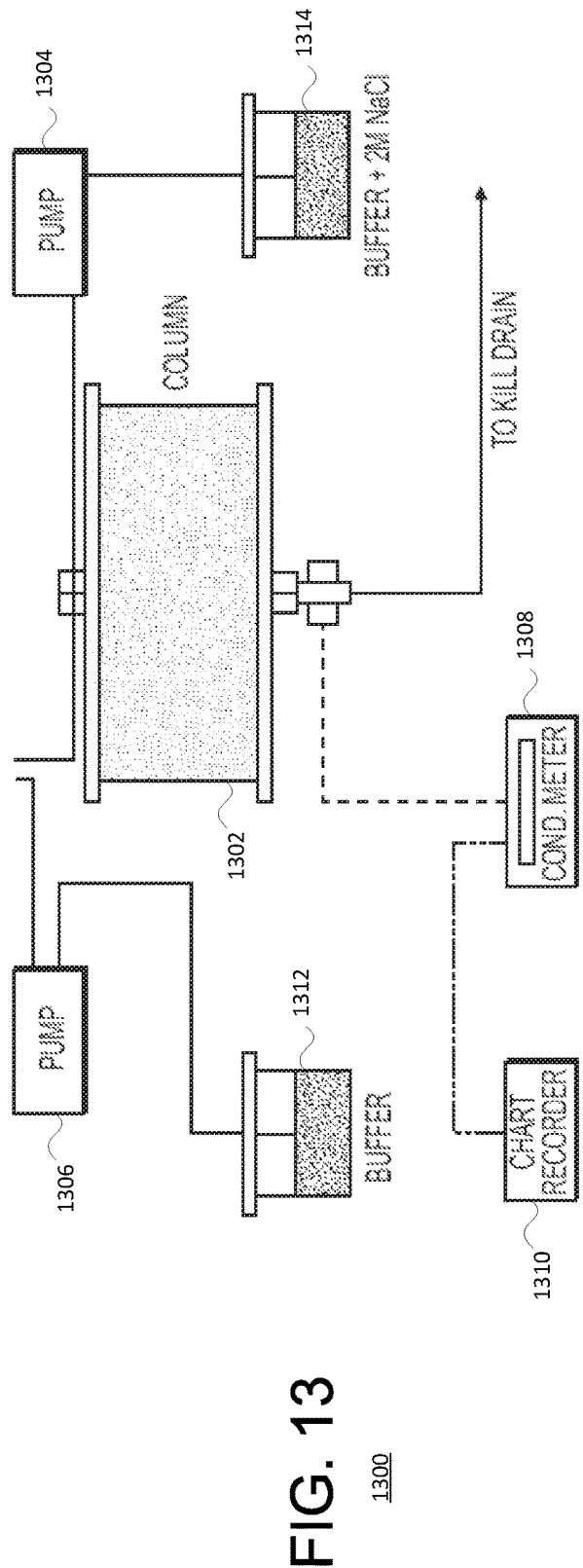
FIG. 13 illustrates a diagram of an example chromatography column system in accordance with one or more aspects of the invention.
Figure 14:
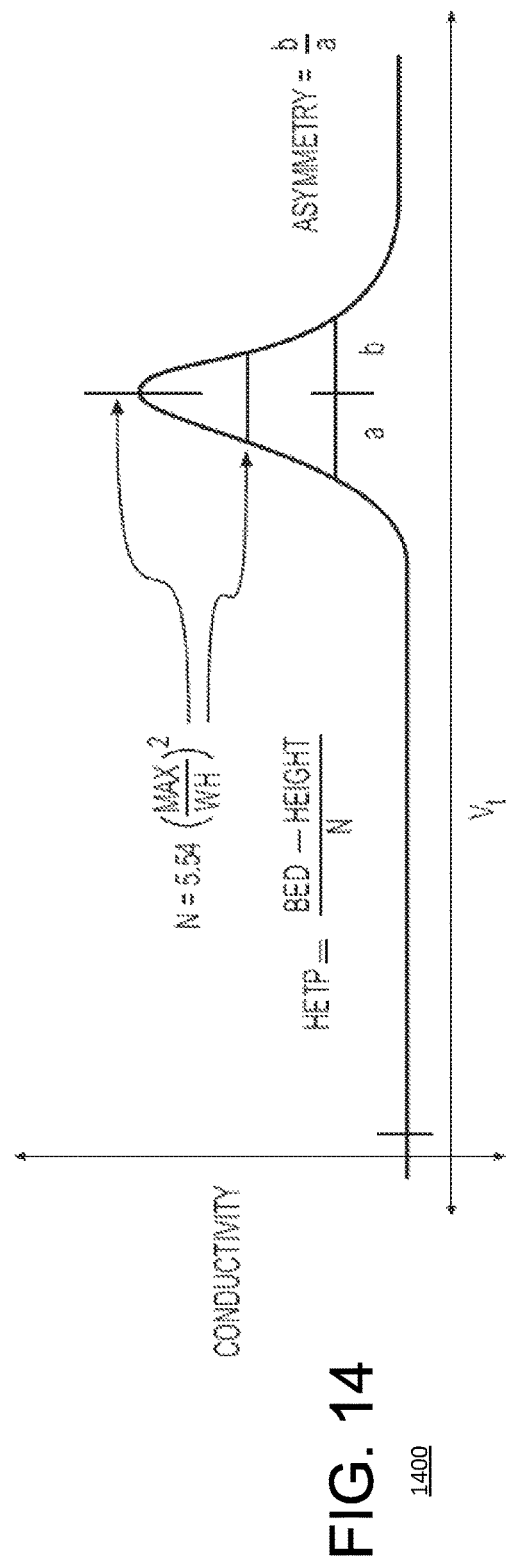
FIGS. 14 to 16 illustrate the application of an HETP control module for real-time analysis of chromatography column packs in accordance with one or more aspects of the invention.
Figure 15:
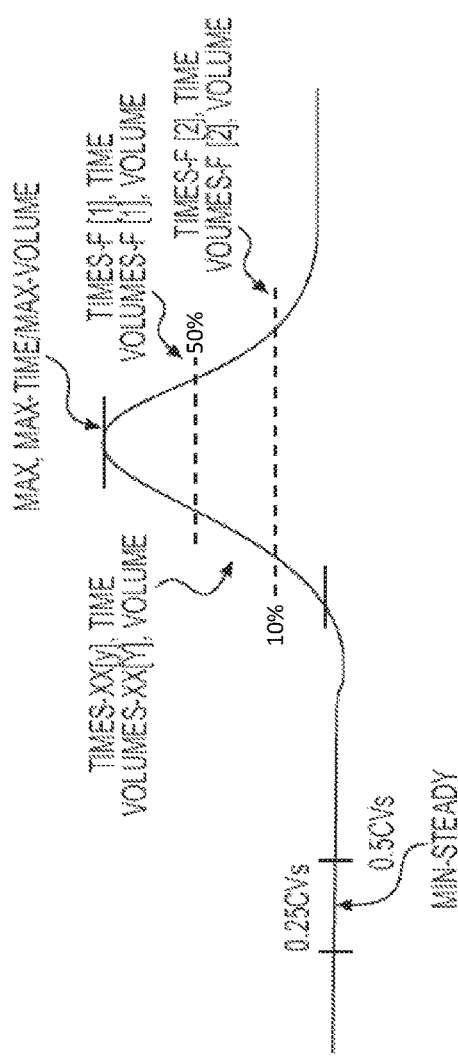
Figure 16:
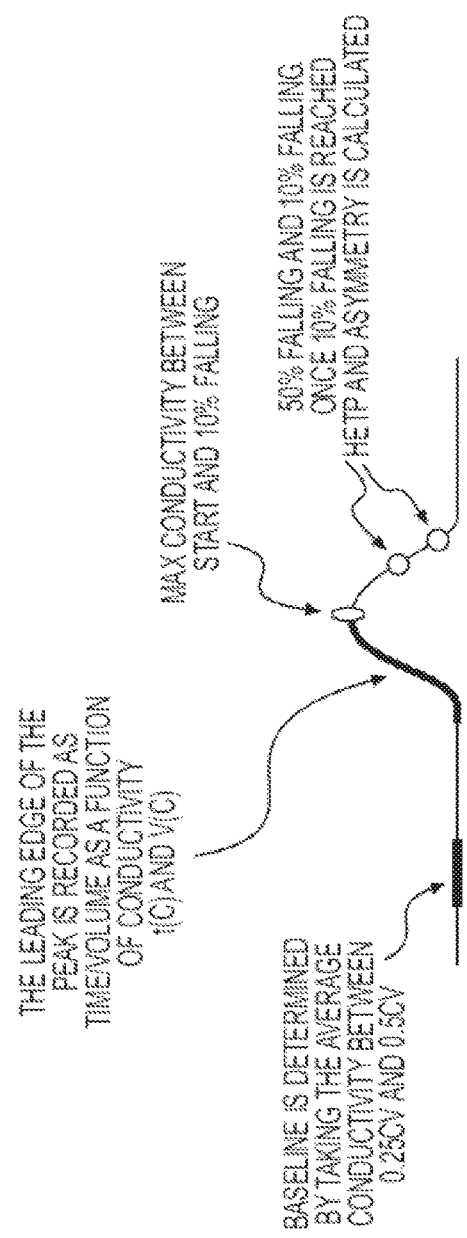

"Height Equivalent of a Theoretical Plate" or "HETP" is the height equivalent of a theoretical plate of a chromatography column, which gives an indication of the uniformity of a packed column to resolve molecules. The smaller the HETP value, the more efficient column packing may be. Asymmetry factor is the measurement used to calculate peak symmetry and should be as symmetrical as possible. FIGS. 12A and 12B illustrate an example of handling chromatography skid HETP calculations in a novel and unique manner in accordance with one or more aspects of the invention. As illustrated, the calculations may be performed by one or more control modules (collectively, an HETP control module) via one or more associated control loops in accordance with certain algorithms. Moreover, FIG. 13 is a diagram of an example chromatography column system, and FIGS. 14-16 illustrate the application of an HETP control module for real-time analysis of chromatography column packs.

In FIG. 12A, the blocks labeled "ACT" each include a set of executable instructions for the control module to perform chromatography skid calculations. For example, in block "ACT1," the MIN and MAX values for conductivity are reset, the calculated times are reset, the timer is enabled and started and the data recording is also enabled. In block "ACT2," the timer is stopped and reset, the data recording disabled, and the CALC-10 and CALC-50 blocks enabled. These two blocks, ACT1 and ACT 2, and the associated actions are based on a positive direction edge trigger (the "PDE1" block), output A, and a negative direction edge trigger (the "NDE1" block), output B (both outputs A and B shown in FIG. 12B), which will be further discussed with respect to FIGS. 13-16. FIG. 12B shows an example algorithm for obtaining the "PDE1" block output A and the "NDE1" block output B. Moreover, FIG. 12B illustrates a "FLTR1" block that takes in input C, which may be conductivity input that is the parameter linked to column outlet conductivity.

In the "MIN-AVG" block in FIG. 12A, the conductivity values are recorded every predetermined period of time, such as every 0.01 second from 0.25 to 0.5 and then an average of the 25 samples is taken and recorded as an internal parameter. In the "RECORD" block, the conductivity values and time/volume are recorded. In the "CALC-10" block, the time/volume at which the rising and falling edge passed through 10 percent of MAX is calculated. Moreover, in the "CALC-50" block, the time/volume at which the rising and falling edge passed through 50 percent of MAX is calculated. In the "CALC-DATA" block, the time/volume of 10 percent rising to MAX and the time/volume to 10 percent falling are calculated.

The calculations performed by the blocks shown in the diagrams of FIGS. 12A and 12B rely on at least various input parameters and/or internal parameters that are recorded. By way of example only, the input parameters may include a "conductivity" input that is linked to column conductivity, a "RUN-CALC" parameter that resets calculation variables, starts timer, and begins data recording when set to "true" and resets timer and disables data recording when set to "false," a "COL-VOL" parameter which is linked to the skid column volume, a "FIQ" parameter that is linked to the skid flow totalizer, a "BED-HEIGHT" parameter that is the height of the column bed, a "COLUMN-VLV" parameter that is linked to the bottom, column inlet valve, and a "CALC-BY-VOL" parameter which is used to select the calculation type (e.g., setting to "false" will by time, setting to "true" will be by volume). The recorded internal parameters, for instance, may include a "FIQ-START" parameter used to record the starting flow totalizer value, a "MIN-STEADY" parameter which is the average of the conductivity baseline, a "MIN-AVG-ARRAY" parameter used to record the baseline conductivity values for the baseline average calculation, a "MAX" parameter that records the maximum conductivity for the duration of the calculation, and a "TIME-MAX" parameter that records the time at which maximum conductivity occurred for the duration of the calculation. These parameters will be further discussed below with respect to FIGS. 14 to 16.

FIG. 13 illustrates a diagram of an example chromatography column system 1300 in accordance with one or more aspects of the disclosure. As shown, for example, the system 1300 includes one or more chromatography columns, such as chromatography column 1302, pumps 1306 and 1304 that are capable of maintaining operational flow rates, conductivity meter 1308, a chart recorder 1310, a conductivity flow cell 1312 and/or 1314, silicone tubing, conductivity standards or equivalent, hose barbs and gaskets, sodium chloride (NaCl), and a filter. After preparing the equipment in the chromatography column system 1300, HETP efficiency and asymmetry can be calculated for real-time analysis of the column packs.

Before calculating the HETP and asymmetry values of the chromatography column, the column may be first leveled in accordance with specified procedures, and hose and miscellaneous valve identifiers may be recorded, as needed, again in accordance with procedures. The column is then equilibrated with a specified HETP buffer solution, and flow at least one column volume (CV) of the HETP buffer at a specified flow rate. Once baseline is achieved, the buffer flow may be stopped. Then, the HETP test is loaded at operation flow rate and the flow of the HETP buffer is resumed at operational flow rates. Once conductivity returns to baseline (e.g., after approximately 1 CV), and from the conductivity readings, the HETP and asymmetry values are calculated, as will be further discussed below.

FIGS. 14-16 illustrate the application of an HETP control module for real-time analysis of chromatography column packs in accordance with one or more aspects of the disclosure. By way of example, FIG. 14 shows a graph 1400 of an equation for calculating HETP and asymmetry on an x-y plot, where the x-axis plots volume/time and the y-axis plots conductivity. As shown in the graph 1400, "WH" represents the width of the peak at 50 percent of maximum conductivity above baseline conductivity, "a" is the difference in time/volume from max peak time/volume minus the time/volume at 10 percent rising, and "b" is the difference in time/volume from 10 percent falling minus the maximum peak time/volume. In that regard, the following values are needed to calculate HETP and asymmetry: baseline conductivity, 10 percent and 50 percent rising times/volumes, maximum time/volume, and 10 percent and 50 percent falling times/volumes. Calculation of the HETP and asymmetry values may be based on time and/or volume.

As discussed above, for internal parameter recording, the following values are recorded in real-time: conductivity baseline average; maximum conductivity and the corresponding time and totalized volume from start; time and totalized volume as a function of conductivity from the baseline to the maximum conductivity; and 10 percent and 50 percent falling time/volume. For example, FIGS. 15 and 16 show the relative positions of these values on the graph 1400. In FIG. 15, the 10 percent and 50 percent on the rising and falling sides of the conductivity peak, and the maximum conductivity and its corresponding time/volume value are illustrated. FIG. 16 illustrates, in part, that the leading edge of the peak is recorded as time/volume as a function of conductivity t(C) and V(C) and that once 10 percent falling has been reached, the HETP and asymmetry is calculated.

By way of the HETP control module example of FIG. 12A, to obtain the baseline conductivity value (MIN-STEADY parameter), the MIN-AVG block records, for instance, 25 conductivity values from the output of the FLTR1 block shown in FIG. 12B every one hundredth of a column volume (CV) from 0.25 to 0.5 CVs. The calculated average of the 25 conductivity values is recorded to the MIN-STEADY parameter after which MIN-AVG calculation terminates. Graphically, as shown in FIGS. 15 and 16, this baseline determination is performed before recording the rising side of the conductivity peak. Thereafter, the RECORD action block in FIG. 12A captures the time and volume at which the conductivity passes through each engineering unit (EU) (e.g., 0.01 mS/cm) from, for instance, 0 to 999 EU. By way of example, the values are recorded in fixed size arrays from TIMES-XX and VOLUMES-XX, as disclosed in FIG. 15. Both arrays may have 1,000 items. Moreover, the values may be only recorded in the arrays when the conductivity value is greater than the recorded maximum value. If the conductivity is greater than the previously recorded maximum, the MAX parameter is overwritten by the current conductivity, the relative time is recorded to TIME-MAX parameter and the relative volume is recorded to the VOLUME-MAX parameter.

With respect to the 10 percent of peak falling time and volume, if the conductivity is less than the MAX parameter but greater than the MIN-STEADY parameter and the value is greater than ((MAX−MIN-STEADY)*0.1+MIN-STEADY), then the elapsed time is recorded to "TIMES-F [2]" and the relative volume is recorded to "VOLUMES-F [2]" by the RECORD action block. With respect to the 50 percent of peak falling time and volume, if the conductivity is less than the MAX parameter but greater than the MIN-STEADY parameter and the value is greater than ((MAX−

MIN-STEADY)*0.5+MIN-STEADY), then the elapsed time is recorded to "TIMES-F[1]" and the relative volume is recorded to "VOLUMES-F[1]" by the RECORD action block.

Once 10 percent falling is reached, the following calculations are performed. The CALC-10 action block in FIG. 12A captures the 10 percent of the peak, ((MAX−MIN-STEADY)*0.1+MIN-STEADY), rising and falling times and volumes, where "TIME-10-FALL" (a calculated internal parameter) is TIMES-F[2], "TIME-10-RISE" (a calculated internal parameter) is determined by linearly interpolating the time between the two neighboring conductivity versus relative time values recorded in TIMES-XX, "VOLUME-10-FALL" (a calculated internal parameter) is VOLUMES-F[2], and "VOLUME-10-RISE" (a calculated internal parameter) is determined by linearly interpolating the time between the two neighboring conductivity versus relative volume values recorded in VOLUMES-XX.

The CALC-50 action block in FIG. 12A captures the 50 percent of the peak, ((MAX−MIN-STEADY)*0.5+MIN-STEADY), rising and falling times and volumes, where "TIME-50-FALL" (a calculated internal parameter) is TIMES-F[1], "TIME-50-RISE" (a calculated internal parameter) is determined by linearly interpolating the time between the two neighboring conductivity versus relative time values recorded in TIMES-XX, "VOLUME-50-FALL" (a calculated internal parameter) is VOLUMES-F[1], and "VOLUME-50-RISE" (a calculated internal parameter) is determined by linearly interpolating the time between the two neighboring conductivity versus relative volume values recorded in VOLUMES-XX.

The CALC-DATA action block shown in FIG. 12A then performs calculation for time and volume based asymmetry and time and volume based HETP. For example, time based asymmetry is calculated as follows:

DELTA-10-RISE-$T$=TIME-MAX−TIME-10-RISE

DELTA-10-FALL-$T$=TIME-10-FALL−TIME-MAX

ASYMM-TIME=DELTA-10-FALL-$T$/DELTA-10-RISE-$T$

In another example, volume based asymmetry is calculated as follows:

DELTA-10-RISE-$V$=VOLUME-MAX−VOLUME-10-RISE

DELTA-10-FALL-$V$=VOLUME-10-FALL−VOLUME-MAX

ASYMM-VOL=DELTA-10-FALL-$V$/DELTA-10-RISE-$V$

In a further example, time based HETP is calculated as follows:

WH-TIME=TIME-50-FALL−TIME-50-RISE

EFF-TIME=5.54*((TIME-MAX/WH-TIME))

HETP-TIME=BED-HEIGHT/EFF-TIME, where BED-HEIGHT is the height of the bed in relevant units.

In yet another example, volume based HETP is calculated as follows:

WH-VOL=VOLUME-50-FALL−VOLUME-50-RISE

EFF-VOL=5.54*((VOLUME-MAX/WH-VOL)$^2$)

HETP-VOL=BED-HEIGHT/EFF-VOL

The parameters "DELTA-10-RISE-T," "DELTA-10-FALL-T," "ASYMM-TIME," "DELTA-10-RISE-V," "DELTA-10-FALL-V," "ASYMM-VOL," "WH-TIME," "EFF-TIME," "HETP-TIME," "WH-VOL," "EFF-VOL," and "HETP-VOL" set forth above are all calculated internal parameters, as shown in FIG. 12B.

Based on at least the calculations disclosed in FIGS. 12A, 12B, and 13-16, the breadth, symmetry (or asymmetry) of the peak of the HETP may be calculated for chromatography skid HETP representation of the quality of the chromatography skid packing execution. In that regard, the operator or user utilizing the control modules associated with the example in FIG. 12 may be able to analyze the symmetry (or asymmetry) of the relevant peaks related to the chromatography skid and subsequently determine whether its performance is being maximized or not maximized enough. Moreover, HETP, peak asymmetry and peak efficiency can be calculated in real-time using the hardware/software that already exists for controlling the chromatography system without having to dedicate special hardware or software.

While FIGS. 12A, 12B, and 13-16 illustrate examples for handling chromatography skid HETP calculations and real-time analysis of the chromatography column packs, it is may be understood that the concept may also apply to one or more control modules implementing a set of executable instructions and/or one or more algorithms to analyze/calculate/manipulate data associated with various types of equipment, such as bioreactors, such as equipment for fermenting, harvesting, equipment for microfiltration and purification (e.g., liquid chromatography skid system), buffer preparation, media preparation, etc.

Figure 17:
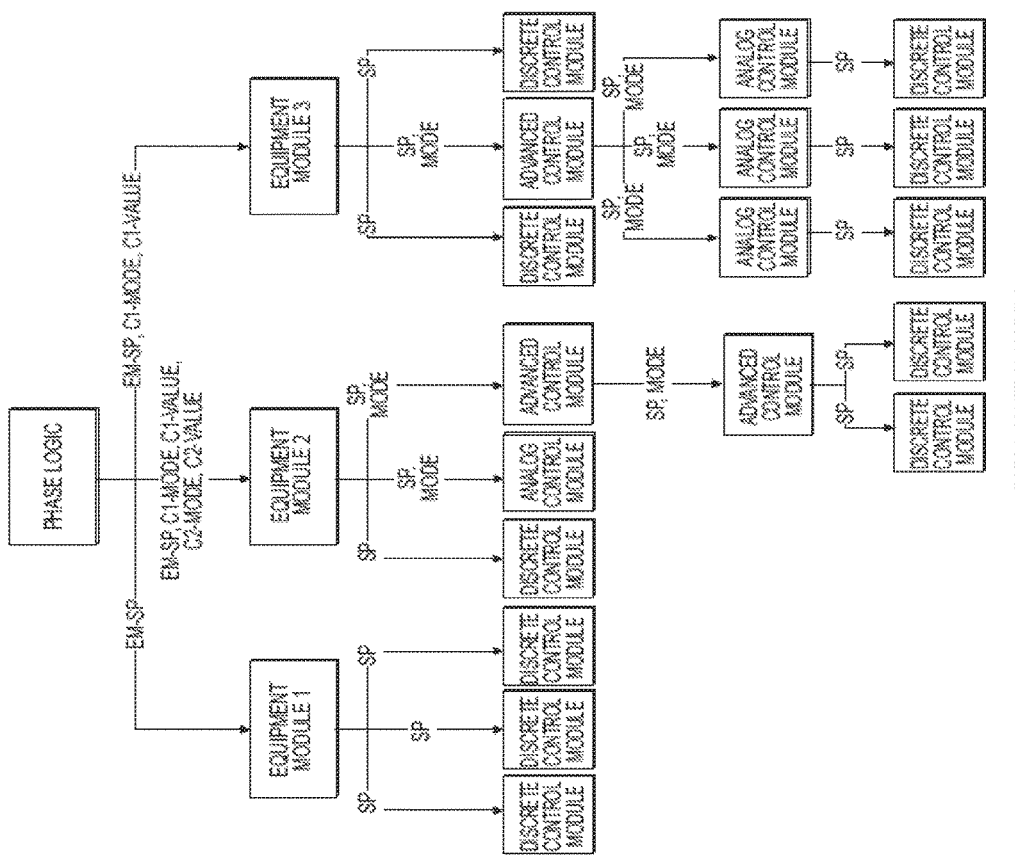
FIG. 17 illustrates a diagram of phase logic, equipment module, and control module relationships in accordance with one or more aspects of the invention.

FIG. 17 is a diagram illustrating the relationships between phase logic, equipment modules, and control modules in accordance with aspects of the invention. FIG. 17, for example, may be in the context of batch control models. As shown, there are various blocks depicting a phase logic, equipment modules, discrete control modules, analog control modules, advanced control modules, etc. Various combinations and designs may be contemplated in order to implement and produce different products using the same equipment and design.

As illustrated in FIG. 17, equipment modules may be logic that controls a group of control modules to perform a specific function, such as transfer into a bioreactor, vent control, etc. Unit classes may be considered to be a group of equipment modules, e.g., a bioreactor. Phases may be sequential logic to control equipment module setpoints, such as set "Transfer Out to Close" parameters and "Vent Control" parameters to VENT. For example, Transfer Out equipment can be set to a CLOSE state, restricting flow from a tank, or the Vent equipment can be set to a VENT state to vent a tank. Phases may be how a bioreactor, for instance, runs in an automated manner. Operations may be sequence of phases to achieve a particular task, e.g., "Fill-Grow-Xfer Operations" runs the "Fill" phase which fills the bioreactor, then the "Grow" phase that supports the culture and the "Xfer" phase to transfer the culture to the next-size bioreactor or other types of harvest systems. Moreover, Unit Procedures and Procedures may be used to control sets of Operations and Unit Procedures, respectively, to achieve a processing step, such as chromatography.

In further examples, there may be naming protocols between field devices and control modules. By way of example only, a control valve may be recognized by the name of "_V-XXXXXX" or "_CV-XXXXXX," such as "LV-383308" or "TCV-383327." In turn, the control module may name the same control valves in this format "_IC-XXXXXX," such as LIC-383308 and TIC-383327, respectively.

The present invention is advantageous in various ways. For example, there is limited material exposure to environmental contaminants. In another example, the present invention is advantageous because it allows for continuous data collection and continuous monitoring and control of system parameters. In addition, it allows for automatic adjustment of cell culture conditions in response to the data collected in order to maintain an optimal environment for maximizing cell growth and production of desired product. Moreover, it also allows for instantaneous response and coordination of devices for equipment control, e.g., processes are on "hold" when conditions are outside of acceptable ranges or an unsafe state has been determined or recognized during processing, providing for return of processes to within process specification, etc.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof. Although the disclosure use terminology and acronyms that may not be familiar to the layperson, those skilled in the art will be familiar with the terminology and acronyms used herein.

What is claimed is:

1. A system for performing real-time analysis on a chromatography column comprising:
   a chromatography column;
   a conductivity meter; and
   at least one processor for executing stored program instructions to:
      measure one or more conductivity values of the chromatography column using the conductivity meter,
      determine a baseline conductivity value by recording a predetermined number of conductivity values from a first column volume to a second column volume and calculating an average of the predetermined number of conductivity values, wherein the baseline conductivity value is the calculated average,
      determine whether a first measured conductivity value is less than a maximum conductivity value and is greater than a 10% peak falling value, and based on the determination, record a time and a column volume corresponding to the first measured conductivity,
      determine whether a second measured conductivity value is less than the maximum conductivity value and is greater than a 50% peak falling value, and based on the determination, record a time and a column volume corresponding to the second measured conductivity,
      detect whether 10% falling of conductivity is reached, and
      based on the detection, calculate one or more of: (i) a time-based asymmetry factor and (ii) a volume-based asymmetry factor or calculate one or more of (i) a time-based Height Equivalent of a Theoretical Plate (HETP) value and (ii) a volume-based HETP value based at least in part on the baseline conductivity value, the times and column volumes of the first measured conductivity and the second measured conductivity, and the maximum conductivity value, and output a control signal for adjusting cell culture conditions in the chromatography column based on the calculation in order to maintain an environment in the chromatography column.

2. The system of claim 1, wherein the 10% peak falling value is equal to:

((the maximum conductivity value−the baseline conductivity value)*0.1)+the baseline conductivity value, and wherein the 50% peak falling value is equal to:

((the maximum conductivity value the baseline conductivity value)*0.5)+the baseline conductivity value.

3. The system of claim 1, wherein the at least one processor further executes stored program instructions to:
   determine whether the maximum conductivity value is greater than a previously recorded maximum value, and
   based on the determination, record a time and a column volume corresponding to the maximum conductivity value.

4. The system of claim 1, wherein the at least one processor further executes stored program instructions to record a time and a column volume for each of the measured one or more conductivity values of the chromatography column, and wherein each time is recorded in a fixed-size time array and each column volume is recorded in a fixed-size volume array.

5. The system of claim 1, wherein the measured one or more conductivity values, when plotted in relation to time or volume, graphically represents a conductivity peak, and the at least one processor further executes stored program instructions to record a plurality of times and column volumes corresponding to each of the respective measured conductivity values on a rising side of the conductivity peak.

6. The system of claim 5, wherein the detection of the 10% falling of conductivity occurs on a falling side of the conductivity peak.

7. A method for performing real-time analysis on a chromatography column, the method comprising:
   measuring, by at least one processor, one or more conductivity values of the chromatography column using a conductivity meter;
   determining, by the at least one processor, a baseline conductivity value by recording a predetermined number of conductivity values from a first column volume to a second column volume and calculating an average of the predetermined number of conductivity values, wherein the baseline conductivity value is the calculated average;
   determining, by the at least one processor, whether a first measured conductivity value is less than a maximum conductivity value and is greater than a 10% peak falling value, and based on the determination, recording a time and a column volume corresponding to the first measured conductivity;
   determining, by the at least one processor, whether a second measured conductivity value is less than the maximum conductivity value and is greater than a 50% peak falling value, and based on the determination, recording a time and a column volume corresponding to the second measured conductivity;
   detecting, by the at least one processor, whether 10% falling of conductivity is reached; and
   based on the detection, calculating, by the at least one processor, one or more of: (i) a time-based asymmetry factor and (ii) a volume-based asymmetry factor or calculating one or more of: (i) a time-based Height Equivalent of a Theoretical Plate (HETP) value and (ii) a volume-based HETP value based at least in part on the baseline conductivity value, the times and column volumes of the first measured conductivity and the second measured conductivity, and the maximum conductivity value, and outputting a control signal for adjusting cell culture conditions in the chromatography column based on the calculation in order to maintain an environment in the chromatography column.

* * * * *